US011875009B2

(12) United States Patent
Ahmadi et al.

(10) Patent No.: US 11,875,009 B2
(45) Date of Patent: Jan. 16, 2024

(54) MULTI-PROCESS ANALYTE MONITORING AND COMMUNICATION SYSTEM

(71) Applicant: EDDII, Inc., New York, NY (US)

(72) Inventors: Farhaneh Ahmadi, New York, NY (US); Patrick Vanegas, Flushing, NY (US); Bhrigu Adlakha, Union City, CA (US)

(73) Assignee: EDDII, Inc., New York, NY (US)

(*) Notice: Subject to any disclaimer, the term of this patent is extended or adjusted under 35 U.S.C. 154(b) by 0 days.

(21) Appl. No.: 17/904,209

(22) PCT Filed: Feb. 12, 2021

(86) PCT No.: PCT/US2021/018001
§ 371 (c)(1),
(2) Date: Aug. 12, 2022

(87) PCT Pub. No.: WO2021/163597
PCT Pub. Date: Aug. 19, 2021

(65) Prior Publication Data
US 2023/0229277 A1    Jul. 20, 2023

Related U.S. Application Data

(60) Provisional application No. 63/108,265, filed on Oct. 30, 2020, provisional application No. 62/977,052, filed on Feb. 14, 2020.

(51) Int. Cl.
*G06F 3/048* (2013.01)
*G06F 16/24* (2019.01)
*A61B 5/145* (2006.01)

(52) U.S. Cl.
CPC .............. *G06F 3/048* (2013.01); *G06F 16/24* (2019.01); *A61B 5/14532* (2013.01)

(58) Field of Classification Search
CPC ...... A61B 5/14532; G06F 16/24; G06F 3/048
See application file for complete search history.

(56) References Cited

U.S. PATENT DOCUMENTS

| | | | | |
|---|---|---|---|---|
| 9,849,364 | B2* | 12/2017 | Tran | G16H 50/20 |
| 9,966,153 | B2* | 5/2018 | Ramachandran | G16Z 99/00 |
| 10,755,806 | B2* | 8/2020 | Ramachandran | G06F 3/0482 |
| 2016/0345874 | A1* | 12/2016 | Raisoni | A61B 5/0022 |
| 2017/0232300 | A1* | 8/2017 | Tran | H04L 67/535 |
| | | | | 434/247 |
| 2021/0093251 | A1* | 4/2021 | Hayter | A61B 5/742 |

OTHER PUBLICATIONS

Chen et al., "Analyzinag System Log Based on Machine Learning Model", International Journal of Network Security, Jan. 11, 2020.*
Wang et al., "Constructing Features for Detecting Android Malicious Applications: Issues, Taxonomy and Directions", May 22, 2019, IEEE Puiblishing.*

* cited by examiner

*Primary Examiner* — Todd L Barker
(74) *Attorney, Agent, or Firm* — Knobbe, Martens, Olson & Bear, LLP

(57) ABSTRACT

Systems and methods are provided for improved analyte processing with data that was captured by analyte monitors. Analyte data entries are processed with multiple child processes and the child processes pass results to a parent process. The parent process aggregates the children results to result in faster processing times. The analyte data is processed in a backend system that is linked to user computing devices with graphical user interfaces.

16 Claims, 27 Drawing Sheets

| Level | Explanation | Blood Glucose Range and Trend | |
|---|---|---|---|
| 1 | Good | R | |
| 2 | Not too worried | R  R | |
| 3 | Right track | L  L  L  H  H  H | |
| 4 | Starting to worry | R  R  H | R  R  L |
| 5 | Worried. Need correction | H | L |

FIG. 7

| Level | Explanation | Blood Glucose Range and Trend | |
|---|---|---|---|
| 6 | Danger - Level 1 | H | L |
| 7 | Danger - Level 2 | H | L |

FIG. 8

MULTI-PROCESS ANALYTE MONITORING AND COMMUNICATION SYSTEM

INCORPORATION BY REFERENCE TO ANY PRIORITY APPLICATIONS

This application claims benefit of U.S. Provisional Patent Application Ser. No. 62/977,052 entitled "MULTI-FACTOR CONTROL ALGORITHMS AND DYNAMIC INTERFACES FOR USE WITH CONTINUOUS ANALYTE MONITOR" filed Feb. 14, 2020, and U.S. Provisional Patent Application Ser. No. 63/108,265 entitled "MULTI-FACTOR CONTROL ALGORITHMS AND DYNAMIC USER INTERFACES FOR USE WITH CONTINUOUS ANALYTE MONITOR" filed Oct. 30, 2020, which are hereby incorporated by reference in their entireties.

Any and all applications for which a foreign or domestic priority claim is identified in the Application Data Sheet as filed with the present application are hereby incorporated by reference under 37 CFR 1.57.

BACKGROUND

An analyte, such as glucose, can be monitored periodically using a continuous glucose monitor.

SUMMARY

The systems, methods, and devices described herein each have several aspects, no single one of which is solely responsible for its desirable attributes. Without limiting the scope of this disclosure, several non-limiting features will now be discussed briefly.

According to various embodiments of the present disclosure, a method for multiprocessing of analyte parameters and analyte monitoring can include: receiving, via a graphical user interface, a request for an analyte history report from a first user computing device; in response to receiving the request for the analyte history report, querying, from an application programming interface, a set of analyte data entries within a time window; calculating a number of child processes to process the set of analyte data entries; determining, from the set of analyte data entries, a first subset of analyte data entries and a second subset of analyte data entries; spawning, based at least in part on the number of child processes, (i) a first child process with the first subset of analyte data entries as first input and (ii) a second child process with the second subset of analyte data entries as second input; receiving (i) first summary data from the first child process and (ii) second summary data from the second child process; combining the first summary data and the second summary data to result in combined summary data; and causing presentation, in the graphical user interface, of the analyte history report comprising at least the combined summary data; receiving, from the application programming interface, a current analyte data entry; causing presentation, in the graphical user interface, of a graphical animated character based at least in part on the current analyte data entry; receiving, via the graphical user interface, user input associated with the graphical animated character; and storing the user input in a database.

In various embodiments, the first child process can be further configured to access data from a secondary data source having behavioral data, and correlate analyte data with the behavioral data within a time window of a data entry from the first subset of analyte data entries.

In various embodiments, the method can include: receiving, via a second graphical user interface, textual user input from a second user computing device; identifying (i) a first user profile associated with the first user computing device and (ii) a second user profile associated with the first user profile, wherein the second user profile is further associated with the second user computing device; determining that the textual user input is directed towards the first user profile; identifying a mediated question associated with the textual user input; causing presentation, via the graphical user interface, of the mediated question on the first user computing device; receiving, via the graphical user interface, a mediated answer in response to the mediated question; and causing presentation, via the second graphical user interface, of an indication of the mediated answer on the second user computing device.

In various embodiments, identifying the mediated question and causing presentation thereof can include translating the textual user input from the first user into the grammatical voice of the graphical animated character and presenting it from the animated character to the second user through the graphical user interface.

In various embodiments, the method can include: generating training data, wherein generating training data further comprises: converting (i) analyte data and (ii) user input associated with at least one of food or exercise to vector data; training a recommendation model using the vector data; providing user input data to the recommendation model; receiving a recommendation from the recommendation model; and causing output, in the graphical user interface, based at least in part on the recommendation.

In various embodiments, the method can include: receiving (i) a challenge setting and (ii) a reward setting; receiving first analyte data associated at least with a first time; determining a first result from the first analyte data according to the challenge setting; receiving second analyte data associated at least with a second time; determining a second result from the second analyte data according to the challenge setting; determining that the first analyte data and the second analyte data collectively satisfy the challenge setting; and in response to determining that the first analyte data and the second analyte data collectively satisfy the challenge setting, causing presentation, in the graphical user interface, of an indication of a reward according to the reward setting.

In various embodiments, the method can include: receiving, via the graphical user interface, textual user input; selecting, from a plurality of textual responses, a first textual response based at least in part on the textual user input; and causing presentation, in the graphical user interface, of the first textual response.

In various embodiments, selecting, from the plurality of textual responses, the first textual response can include: providing the textual user input to a chat classifier; and receiving an indication of the first textual response from the chat classifier.

In various embodiments, the method can include: generating labels from (i) a plurality of questions and (ii) a plurality of answers; converting the plurality of questions to question vector data; and training the chat classifier using the question vector data and the labels.

According to various embodiments of the present disclosure, a system can include: a memory device configured to store instructions; and a hardware processor configured to execute the instructions to cause the hardware processor to: receive, via a graphical user interface, a request for an analyte summary report from a first user computing device; in response to receiving the request for the analyte summary report, query, from an application programming interface, a set of analyte data entries within a time window; calculate a number of child processes to process the set of analyte data entries; determine, from the set of analyte data entries, a first subset of analyte data entries and a second subset of analyte data entries; spawn, based at least in part on the number of child processes, (i) a first child process with the first subset of analyte data entries as first input and (ii) a second child process with the second subset of analyte data entries as second input; receive (i) first summary data from the first child process and (ii) second summary data from the second child process; combine the first summary data and the second summary data to result in combined summary data; and cause presentation, in the graphical user interface, of the analyte summary report comprising at least the combined summary data; receive, from the application programming interface, a current analyte data entry; and cause presentation, in the graphical user interface, of a graphical character based at least in part on the current analyte data entry.

In various embodiments, the system can further be configured to: receive, via a second graphical user interface, textual user input from a second user computing device; identify (i) a first user profile associated with the first user computing device and (ii) a second user profile associated with the first user profile, wherein the second user profile is further associated with the second user computing device; determine that the textual user input is directed towards the first user profile; identify a mediated question associated with the textual user input; cause presentation, via the graphical user interface, of the mediated question on the first user computing device; receive, via the graphical user interface, a mediated answer in response to the mediated question; and cause presentation, via the second graphical user interface, of an indication of the mediated answer on the second user computing device.

In various embodiments, the system can further be configured to: generate training data, wherein generating training data further comprises: converting (i) analyte data and (ii) user input associated with at least one of food or exercise to vector data; train a recommendation model using the vector data; provide user input data to the recommendation model; receive a recommendation from the recommendation model; and cause output, in the graphical user interface, based at least in part on the recommendation.

In various embodiments, the system can further be configured to: receive (i) a challenge setting and (ii) a reward setting; receive first analyte data associated at least with a first time; determine a first result from the first analyte data according to the challenge setting; receive second analyte data associated at least with a second time; determine a second result from the second analyte data according to the challenge setting; determine that the first analyte data and the second analyte data collectively satisfy the challenge setting; and in response to determining that the first analyte data and the second analyte data collectively satisfy the challenge setting, cause presentation, in the graphical user interface, of an indication of a reward according to the reward setting.

In various embodiments, the system can further be configured to: receive, via the graphical user interface, textual user input; select, from a plurality of textual responses, a first textual response based at least in part on the textual user input; and cause presentation, in the graphical user interface, of the first textual response.

In various embodiments, selecting, from the plurality of textual responses, the first textual response can include: providing the textual user input to a chat classifier; and receiving an indication of the first textual response from the chat classifier.

In various embodiments, the system can further be configured to: generate labels from (i) a plurality of questions and (ii) a plurality of answers; convert the plurality of questions to question vector data; and train the chat classifier using the question vector data and the labels.

According to various embodiments of the present disclosure, a system for evaluating and enhancing user analyte levels, the system can include: a memory device configured to store instructions; and a hardware processor configured to execute the instructions to cause the hardware processor to: accept input from an analyte monitor taking current analyte data from a user; solicit and accept text input from the user, independent of the analyte data; evaluate combinations of text input and analyte data to provide calibrated behavioral incentives to the user; establish in computer memory a data structure for correlating input from the text input from the user and text or other visual outputs to the user, according to the calibrated behavioral incentives; and cause presentation, in a user interface, a virtual world including: a communicating character configured to engage with the user to solicit and accept the text input and provide at least some of the calibrated behavioral incentives; and animations of the communicating character and a virtual world environments for that character, said animations and environments configured to convey to the user whether user action is needed to improve subsequent analyte data readings taken by the analyte monitor.

In various embodiments, the system can further include: a framework for user interaction comprising logic, libraries, and an artificial intelligence model configured to learn the vocabulary and habits of a particular user, store data that records what it has learned, and therefore more quickly interpret inputs from the user to more efficiently recommend action to improve an analyte level.

In various embodiments, the system can further be configured to recognize user-specific terminology that has previously been correlated with low analyte levels and recommend a user-preferred food to increase the analyte level.

In various embodiments, the system can be further configured to use correlated data from a large sample of other users to make recommendations to specific users.

According to various embodiments of the present disclosure, a method can include: integrating an application with a user's continuous glucose monitor to accept current glucose levels of a user; using games and virtual objects to incentivize user behavior to improve glucose levels if needed; employing an animated character to gather information from the user relevant to glucose levels and metabolism; and conveying glucose information to the user regarding current glucose levels through messages from the character and the appearance of the virtual world.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the aboveand/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. The following is a brief description of each of the drawings.

FIGS. 7 and 8 illustrate a table that summarizes levels and indicators related to analyte monitoring, according to some embodiments of the present disclosure.

DETAILED DESCRIPTION

A medical device (e.g., a continuous glucose monitor or CGM) can capture analyte parameters from a user and the analyte parameters can be received by a system. An analyte parameter data set can include thousands or data entries. Analysis on the analyte data entries may be desirable. However, due to the sheer volume of data entries, data processing of the data entries may be relatively slow. For example, without the improvements described herein, processing thousands of data entries can take approximately one minute or longer, which may be an unacceptable amount of time for interactive user interfaces.

Disclosed herein are systems and methods that may be used to advantageously improve processing of analyte parameters. As described above, some existing methods for processing analytes may be relatively slow. Instead of processing thousands of data entries with a single process, a processing and communication system can use multiprocessing to process the data entries with multiple child processes and aggregate the results from the child processes to result in faster processing times. Instead of processing times taking one minute or longer, the improved concurrent multiprocessing techniques described herein can cut the processing time down to 3-4 seconds in some instances. The mechanisms for concurrent multiple processing techniques can also advantageously avoid concurrent processes from simultaneously processing the same data entries.

Figure 1A:
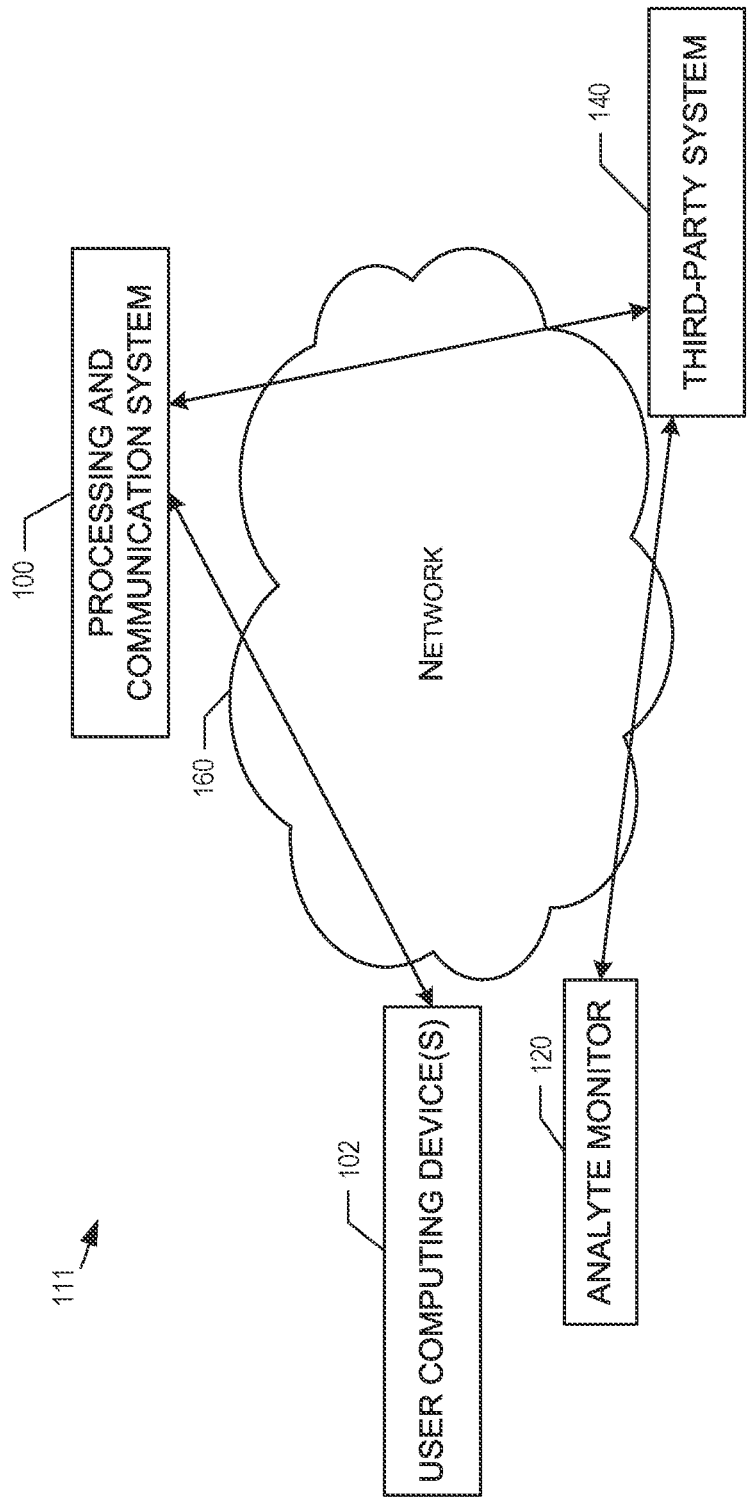
FIGS. 1A and 1B illustrate a processing and communication system, according to some embodiments of the present disclosure.

FIG. 1A illustrates a processing and communication system 100, according to some embodiments of the present disclosure. In the embodiment of FIG. 1A, the computing environment 111 can include a network 160, a processing and communication system 100, one or user computing devices 102, an analyte monitor 120, and a third-party system 140. The analyte monitor 120 can be a continuous glucose monitor or CGM. An example analyte monitor 120 can be a monitor that is a part of the Dexcom glucose monitoring system. Various communications between these devices are illustrated. For example, the analyte monitor 120 can provide analyte data to the third-party system 140. The processing and communication system 100 can communicate with the third-party system 140 to retrieve analyte data. The user computing device 102 may send user input to the processing and communication system 100. The user computing device 102 may enable a user to interact with a graphical user interface, such as the graphical user interfaces described herein. Multiple user computing devices 120 may communicate with one another via the processing and communication system 100.

Figure 1B:
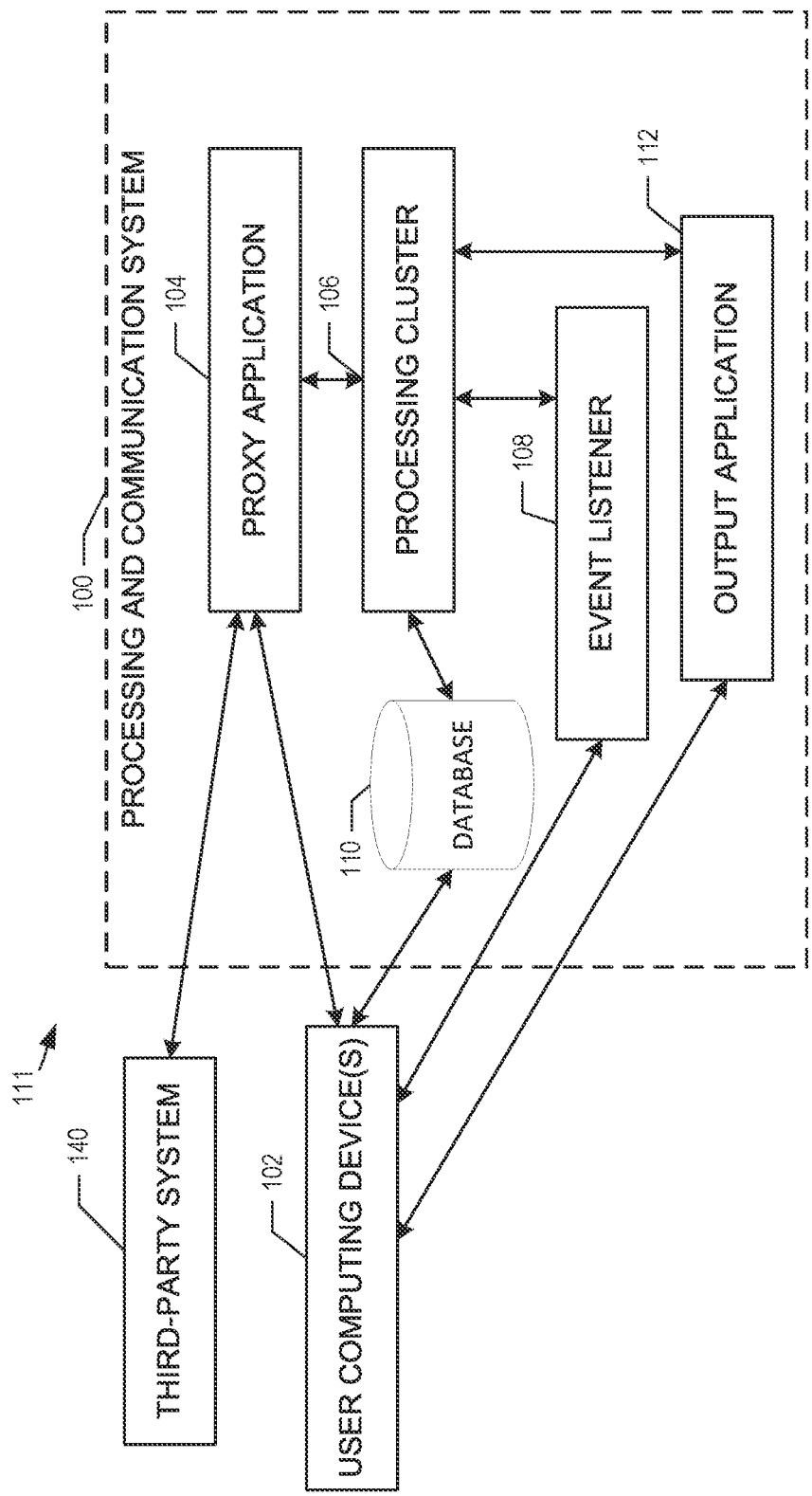

FIG. 1B illustrates a processing and communication system 100, according to some embodiments of the present disclosure.

The processing and communication system 100 can receive analyte data (such as glucose values) from the third-party system 140 for various purposes. The processing and communication system 100 can include a proxy application 104, a processing cluster 106, a database 110, an event listener 108, and an output application 112. In some embodiments, the proxy application 104, the processing cluster 106, the database 110, the event listener 108, and the output application 112 can be hosted in one or more hosted computing environments. An example processing cluster 106 is an Apache Kafka cluster. Examples database 110 include relational databases, in-memory databases (such as node-cache), and/or a Redis database. The proxy application 104 can call an application programming interface (API) of the third-party system 140 to receive analyte data. In some embodiments, the proxy application 104 can regularly poll the third-party system 140 (such as every five minutes). An example data format for the analyte data is a JavaScript Object Notation (JSON) data format.

The data can include a current analyte data entry (such as a glucose value) and trend data. In some embodiments, the API call can be made at regular intervals (such as 5 minute intervals) for every user using a user application on a user computing device 102. Moreover, in some embodiments, the API call may only be made while the user application is in the foreground. In some embodiments, the proxy application 104 can continuously monitor the application and stop making the API calls when either the user application moves to the background or the application quits. The proxy application can make calls to partner APIs. The received data may be transient and can be queried as needed to display it in the user application and/or for performing and displaying aggregated output.

When the application moves to a background state, the application can call an asynchronous endpoint in the proxy application so that notifications can be sent to the user application and/or the user computing device 102 in case a corresponding analyte value goes above or below the maximum and minimum analyte value, which can be set by a user. For example, if the maximum analyte value is 200, then if their analyte goes above 200 and the user application is currently not running, then a notification can be sent to the application and/or the user computing device 102.

The asynchronous backend application calls the same third-party API endpoint to get the analyte value and writes it to the processing cluster 106. The processing cluster 106 can in turn write analyte data to the database 110. The event listener 108 listens to the events in processing cluster 106 to find out if a notification has to be sent to the user (for example, when their analyte value goes above a certain value). The event listener 108 continuously polls the processing cluster 106. If there are new events, the event listener 108 will process them. Events can be related to the users. Events can be in a JSON format. The output application 112 can cause data to be presented in the user computing device 102, such as summary reports. If the event is in the wrong format, an error can be sent to the sender. In some embodiments, the processing cluster 106 can handle millions of messages per hour and can process notifications for thousands of users.

Users can provide data through the user application. For example, a user can create a user profile with their using their email address, along with the email address of their parent (or guardian). This information can be stored in the database 110. In addition to the data collected during sign up, users are also able to update information in their profile by going to settings. Users are able to enter information such as their name and age. Within the user application, users are also able to enter information about their activities, feelings, medications and food intake to earn rewards. This information can also stored in the database 110 and can be used to generate health summary reports. An example summary report is an analyte history report.

In some embodiments, the processing and monitoring system 100 and/or components thereof are implemented by one or more virtual machines implemented in a hosted computing environment. The hosted computing environment may include one or more rapidly provisioned and/or released computing resources. The computing resources may include hardware computing, networking and/or storage devices configured with specifically configured computer-executable instructions. Hosted computing environments can be referred to as "cloud computing" environments.

Figure 2:
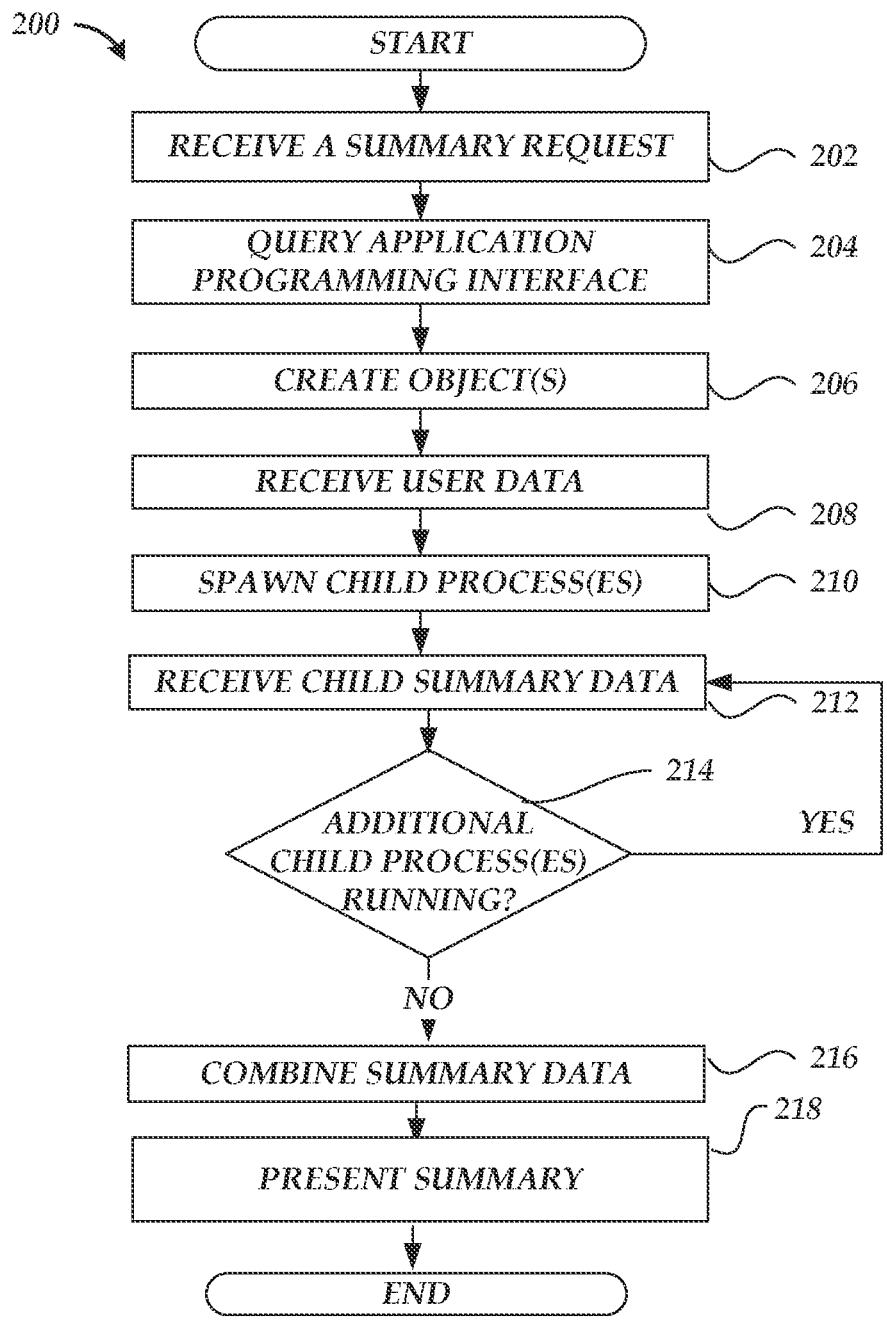
FIG. 2 is a flowchart of an example multiprocessing analyte method, according to some embodiments of the present disclosure.

FIG. 2 is a flowchart of an example multiprocessing analyte method 200, according to some embodiments of the present disclosure. Although the method 200 is described in conjunction with the systems of FIGS. 1A-1B, any system configured to perform the method, in any order, is within the scope of this disclosure. The method 200 may be performed by the various components of the processing and communication system 100 of FIGS. 1A-1B as discussed herein. Depending on the embodiment, the method 200 may include fewer or additional blocks and/or the blocks may be performed in an order different than is illustrated.

At block 202, a summary request can be received. For example, a user using the user application on the user computing device 102 can request a summary report, such as via a graphical user interface. The proxy application 104 can receive the request.

At block 204, an application programming interface can be queried. In particular, the proxy application 103 can query the application programming interface of the third-party system 140. Example input to the application programming interface can include: a user identifier (such as an email), a start date/time, and an end date/time, which can query the API for analyte records from the start date/time to the end date/time for the user. Example analytes can be estimated glucose values or "egvs" or "EGVS." Example output can be shown in the below Table 1, which can be in a JSON data format.

TABLE 1

```
{
  "egvs": [
    {
      "Egv":
        120,
          "Time": "2021-02-01T18:26:08",
    }
  ]
}
```

At block 206, one or more objects can be created. For example, the processing cluster 106 can create one or more objects. The processing cluster 106 can create an object to store aggregated results (such as the example childMetrics object shown in the below Table 2).

TABLE 2

```
childMetrics {
    topFourMoods,
    totalActivity,
    glucoseMetrics:
    {
      inRangeCount: 0,
      lowRangeCount: 0,
      highRangeCount: 0,
      entries: 0,
    },
    averages: {
      avgEgvAfter2HoursActivity: 0,
      avgEgvAfter2HoursTopMood: 0,
      avgEgvAfter2HoursCarbs: 0,
    },
}
```

The processing cluster 106 can create an object to store summary data (such as sums and counts) needed to calculate statistical measures such as averages. Such an example object is shown in the below Table 3.

TABLE 3

```
sums {
    sumOfEgvsRelatingToActivity: 0,
    sumOfEgvsRelatingToTopMood: 0,
    sumOfEgvsRelatingToCarbs: 0,
```

TABLE 3-continued

```
        countOfEgvsFollowedByActivity: 0,
        countOfEgvsFollowedByTopMood: 0,
        countOfEgvsFollowedByCarbs: 0,
    }
```

At block 208, user data can be received. For example, the processing cluster 106 can receive user data from the database 110. An example query of the database 110 for user data (such as user high and lows) is shown below in Table 4, where $1 represents a user identifier.

TABLE 4

```
SELECT
glucose_low AS "lowRange", glucose_high AS "highRange"
FROM profile
WHERE user_id = (SELECT id FROM users WHERE email = $1)
```

Additional user data can include moods data. Another example query of the database 110 for user data (such as top four moods) is shown below in Table 5, where $1, $2, and $3 represent the user's identifier, a start date/time, and an end data date/time.

TABLE 5

```
SELECT mood, COUNT(1)::int AS frequency FROM feeling
    WHERE user_id = (SELECT id FROM users WHERE email = $1)
AND created_at >= $2::date
    AND created_at <= $3::date
    GROUP BY mood
    ORDER BY frequency DESC LIMIT 4;
```

At block 210, one or more child processes are spawned. In particular, a parent process in the processing cluster 106 can spawn one or more children process. For example, a "chunk" can be defined as number of rows or data entries to be processed by a single child process. An example chunk value can be 500. The parent process can determine a number of child processes by dividing the number of data entries by the "chunk" value, or more specifically, number of child processes=ceiling(number of rows/chunks). The parent process can loop from 0 to number of child processes and fork a child process in each iteration, while assigning each subset of analyte data entries to respective child processes. 11. Through each iteration of the loop in the parent process, the parent process collects the process ids of each child process into an array of process ids. The parent process sends a message with the user identifier, chunk of data, high range, and low range to the newly created child process within the same iteration. An example message is shown below in Table 6.

TABLE 6

```
child.send({
    Email,
    data: data.slice(j,j+chunk), highRange,
    lowRange
})
```

At block 212, summary data can be received. For example, the parent process in the processing cluster 106 can receive summary data from child processes. The parent process can listen for an event message to collect the results of a child process and accumulate the results in the one or more objects, such as the childMetrics and/or sums objects. An example message handler in this regard is shown below in Table 7.

TABLE 7

```
child.on('message', (msg) => {if (msg) {
childMetrics["glucoseMetrics"]["inRangeCount"]    +=    msg["inRangeCount"];
childMetrics["glucoseMetrics"]["lowRangeCount"]   +=    msg["lowRangeCount"];
childMetrics["glucoseMetrics"]["highRangeCount"]  +=    msg["highRangeCount"];
childMetrics["glucoseMetrics"]["entries"]         +=    msg["entries"];
sums["sumOfEgvsRelatingToActivity"] += msg["sumOfEgvsRelatingToActivity"];
sums["sumOfEgvsRelatingToTopMood"]                                        +=
msg["sumOfEgvsRelatingToTopMood"]; sums["sumOfEgvsRelatingToCarbs"]       +=
msg["sumOfEgvsRelatingToCarbs"]; sums["countOfEgvsFollowedByActivity"]    +=
msg["countOfEgvsFollowedByActivity"];
sums["countOfEgvsFollowedByTopMood"]                                      +=
msg["countOfEgvsFollowedByTopMood"];
```

The child process can receive a message from the parent process, which can be shown in the below Table 8.

TABLE 8

```
process.on('message', async (msg) => { email ← msg.email;
    data ← msg.data;
    result ← await getAvgChunk(data, db, email, lowRange, highRange);
    process.send(result);
    process.exit( );
}
```

An accumulation function can (such as getAvgChunk) can accumulate the summary values in the one or more accumulation objects. The accumulation function can loop through the data array with the egvs and can query the database 110 with the given parameters to calculate combined summary data. Example first summary data can include a total exercise time (minutes) 2 hours after the current egv time property. A corresponding query that can be used by a child process is shown below in Table 9, where $1, $2 relate to the user's identifier and egv's time value, respectively.

TABLE 9

```
SELECT carbs FROM metrics
WHERE user_id = (SELECT id FROM users WHERE email = $1)
AND created_at::date >= $2::date
AND created_at::date <= $2::date + interval '2 hour' AND carbs IS
NOT NULL AND carbs != 0;
```

Example second summary data can include a total count of records with the top mood 2 hours after current egv time property. A corresponding query that can be used by a child process is shown below in Table 10, where $1, $2, and $3 represent the top mood, user's identifier, and the egv time.

TABLE 10

SELECT mood FROM feeling WHERE mood = $1
AND user_id = (SELECT id FROM users WHERE email = $2) AND created_at::date >= $3::date
AND created_at::date <= $3:: date + interval '2 hour';

Additional example summary data that can be calculated by child processes can include: (i) count of egv data points followed by an activity; (ii) count of egv data points followed by exercise (minutes); (iii) count of egv data points followed by top mood/feeling; and (iv) count of egvs that are in range/above high range/below low range.

Once a child process finishes this aggregation, it can send its results back to the parent. For example, the child process can send data through the "message" event using process.send(data) and stop itself from executing.

At block 214, it can be determined whether any child processes are still running. For example, the parent process can initialize a while loop. The parent process can loop through the childProcesses array and set isRunning=true if there is a process id that is still running using a utility method where process.kill(process-id, 0) is called on each process of the childProcesses, sending a signal of 0 that checks if the process is still active or not. If isRunning is true, sleep the central process for 100 ms to wait for the child processes to finish and go to the next iteration of the while loop and repeat. If isRunning is false, the parent process can break out of the while loop.

At block 216, summary data can be combined. In particular, the parent process can combine the summary data. Once out of the while loop, the child processes have finished and the one or more objects should now have the accumulated results of all of the child processes. The parent process can calculate statistical measures, such the averages needed for childMetrics shown in Table 11 below.

TABLE 11 childMetrics["averages"]["avgEgvAfter2HoursCarbs"] = ⌊
sums["sumOfEgvsRelatingToActivity"] /
sums["countOfEgvsFollowedByActivity"] ⌋
childMetrics["averages"]["avgEgvAfter2HoursTopMood"] = ⌊
sums["sumOfEgvsRelatingToTopMood"]/
sums["countOfEgvsFollowedByTopMood"]⌋
childMetrics["averages"]["avgEgvAfter2HoursActivity"]=
⌊Math.floor(sums["sumOfEgvsRelatingToCarbs"]/
sums["countOfEgvsFollowedByCarbs"])⌋

At block 218, the combined data can be presented. In particular, the output application 112 can transmit the combined data to be presented in a graphical user interface of the user computing device 102 (such as a weekly report), as described herein. An example summary report can include one or more components. A report can include a header where the user can toggle between "1 day", "1 week", "2 weeks", and "1 month" time intervals to view data from a selected interval in the past. The report can include a chart (such as a pie chart) displaying the average egv value over a time period that shows the user what percentage of the egvs were in range (colored green on the pie chart), below the low range (colored red), and above the high range (colored yellow). The report can include another chart displaying the total amount of exercise time the user has had over the selected time interval along with the average egv of data points aggregated 2 hours after the user has recorded their exercise time. The report can include another chart displaying the top four moods that the user has had over the selected time interval, how frequent the user has felt those moods, and the average egv of data points aggregated 2 hours after the user has recorded their exercise time. The report can include another chart displaying the total amount of carbohydrates the user has entered in the selected time interval and the average egv of data points aggregated 2 hours after the user has recorded an entry of carbohydrate intake data.

Figure 3:
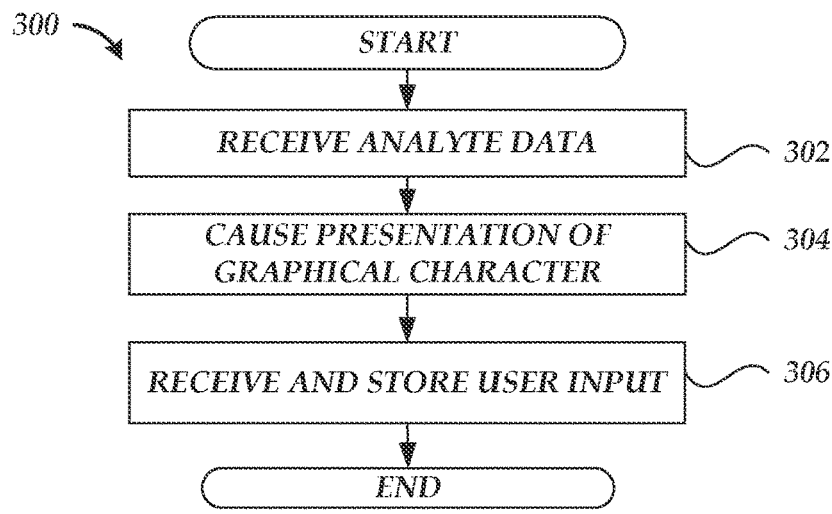
FIG. 3 is a flowchart of an example graphical user interface method, according to some embodiments of the present disclosure.

FIG. 3 is a flowchart of an example graphical user interface method 300, according to some embodiments of the present disclosure. Although the method 300 is described in conjunction with the systems of FIGS. 1A-1B, any system configured to perform the method, in any order, is within the scope of this disclosure. The method 300 may be performed by the various components of the processing and communication system 100 of FIGS. 1A-1B as discussed herein. Depending on the embodiment, the method 300 may include fewer or additional blocks and/or the blocks may be performed in an order different than is illustrated.

At block 302, analyte data can be received. As described herein, analyte data, such as a current analyte data entry, can be received from the API of the third-party system 140, which can be further processed by the processing cluster 106. At block 304, a graphical character can be presented in a graphical user interface. For example, the user application can present a graphical character based at least in part on the current analyte data entry. As described herein, the graphical character can be animated or presented to reflect a user's current analyte status. At block 306, user input can be received and stored. For example, the user application can receive user input that relates to the user's mood, food intake, exercise, etc. and store the data in the database 110. In some embodiments, the received user input can be received in relation to the graphical character, such as by chatting with the character or selecting user interface elements associated with the graphical character.

Figure 4:
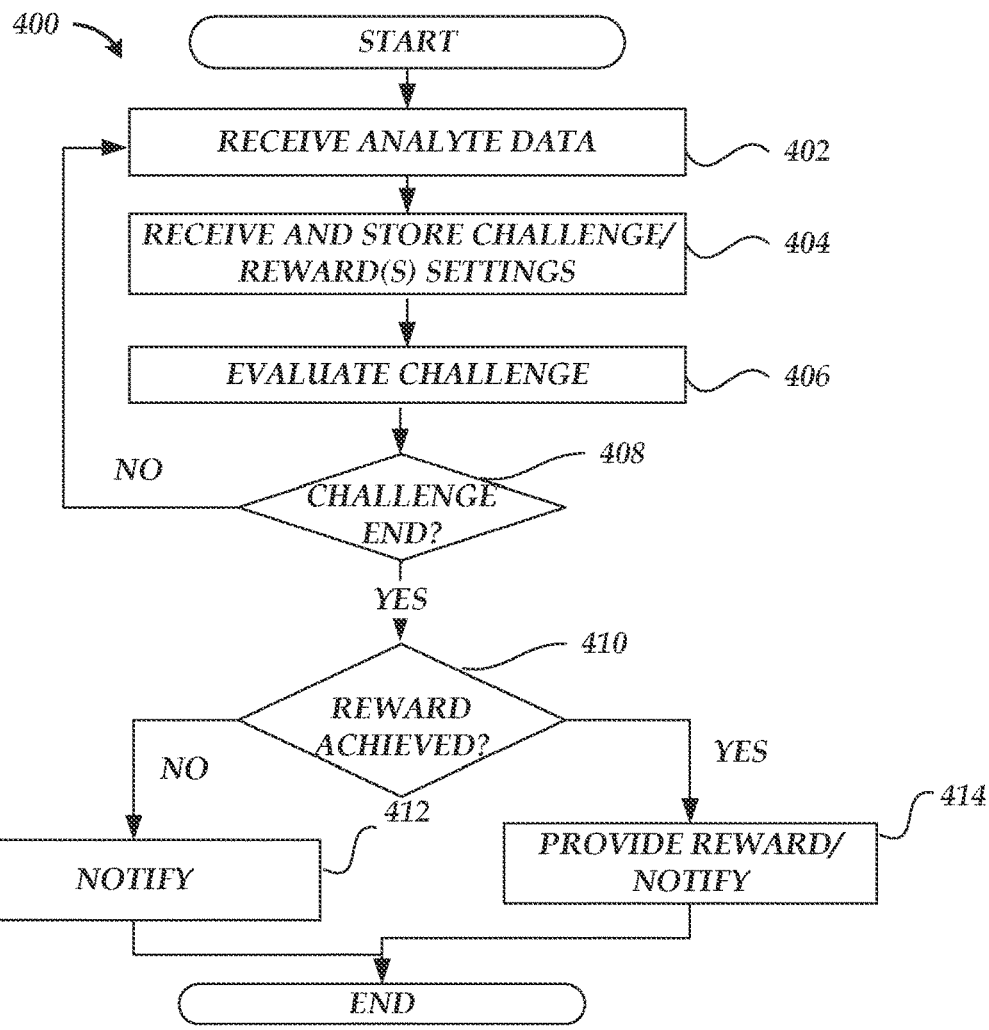
FIG. 4 is a flowchart of an example challenge and reward method, according to some embodiments of the present disclosure.

FIG. 4 is a flowchart of an example challenge and reward method 400, according to some embodiments of the present disclosure. Although the method 400 is described in conjunction with the systems of FIGS. 1A-1B, any system configured to perform the method, in any order, is within the scope of this disclosure. The method 400 may be performed by the various components of the processing and communication system 100 of FIGS. 1A-1B as discussed herein. Depending on the embodiment, the method 400 may include fewer or additional blocks and/or the blocks may be performed in an order different than is illustrated.

Figure 13:
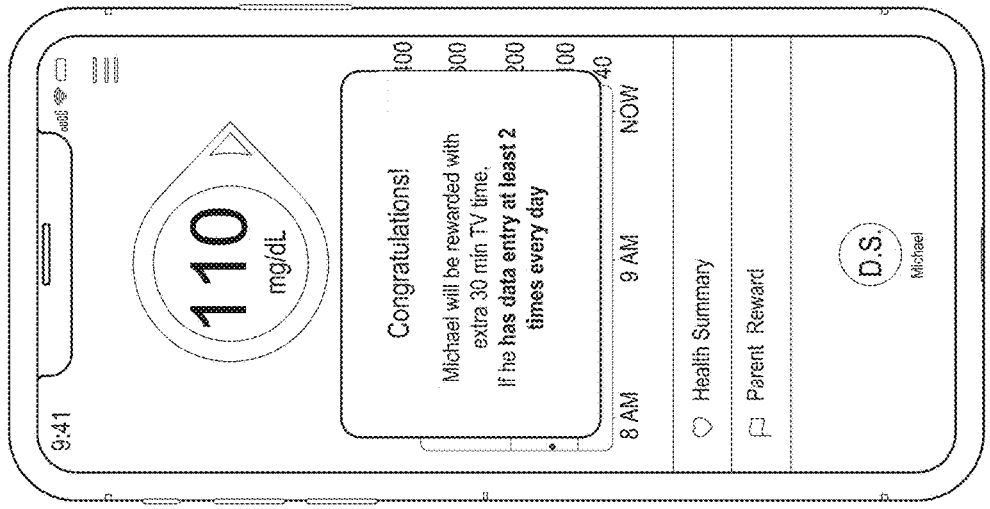
Figure 13:
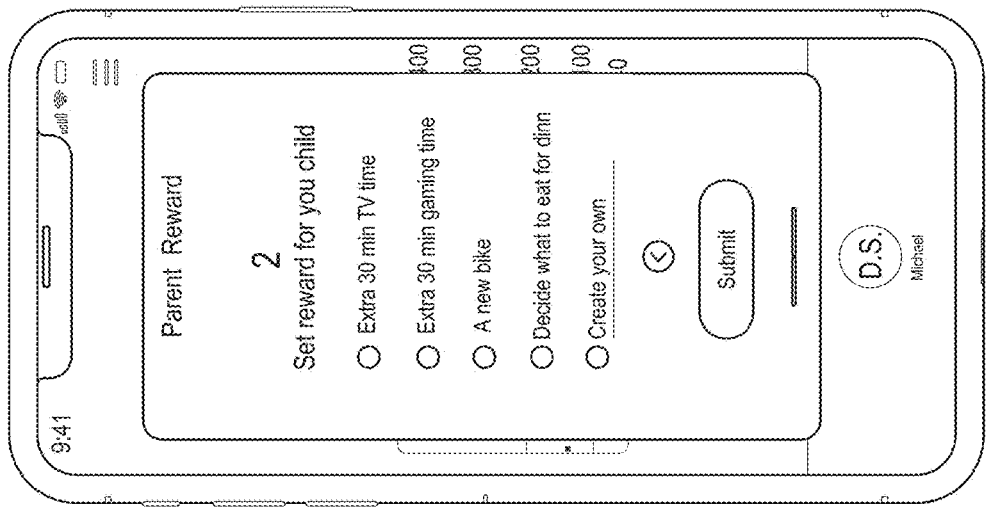
Figure 13:
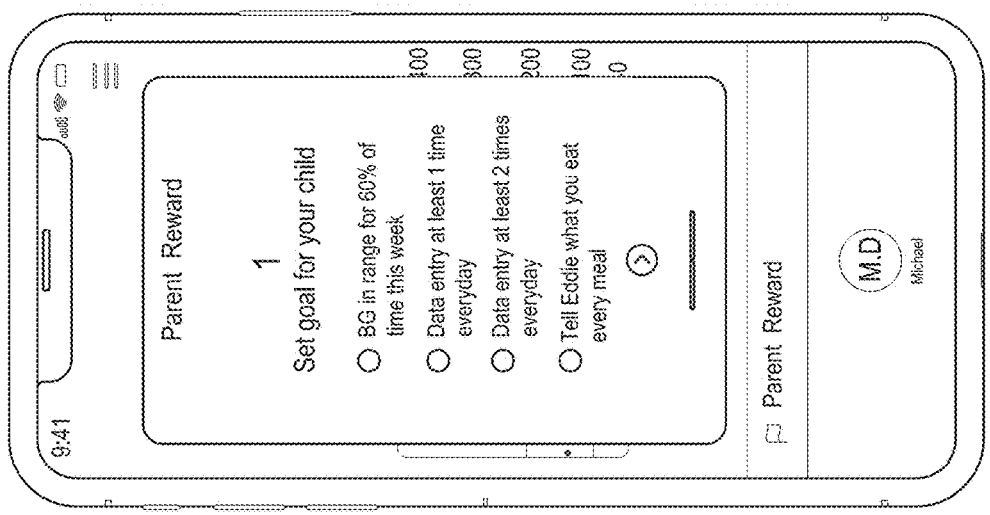

At block 402, analyte and analyte-related (such as user input) data can be received as described herein. At block 404, challenge and reward settings can be received. The system can include parent-child reward features, whereby a parent of a child with diabetes can set daily and weekly food, exercise and medication goals for their child (e.g., eating their meals three times a day, taking their medication on time, or exercising a certain amount of time), and this can translate into real-life rewards, such as extra TV time or a physical reward from the parent (e.g., a bike). In some embodiments, the parent can enter their own reward of choice. Additional parent-child challenge and reward settings are shown in FIG. 13.

At block 406, a challenge can be evaluated. For example, the processing cluster 106 can evaluate challenges (such as daily or weekly) for users. For a daily challenge, the processing cluster 106 can check if a user has satisfied confirming that the user drank water four times a day, exercised for twenty minutes, kept their glucose level below a threshold or within a range, etc. For a longer challenge (such as a weekly challenge), the processing cluster 106 can check if a user has satisfied multiple criteria or criteria that requires determining accumulated data. For example, a user may have to keep their analyte levels within a range for the whole week, and the processing cluster 106 can check compliance with the challenge or calculate summary data on an incremental basis (such as once a day). At block 408, it can be determined whether the challenge has ended. In particular, the processing cluster 106 can determine whether challenges have reached their end point by which ultimate compliance can be checked. If the challenged has not ended, then the method 400 can return to block 402 to receive more analyte and analyte-related data. Otherwise, the method 400 can proceed to block 410 to determine whether the reward has been achieved 410. If the reward has been achieved, the method 400 can proceed to block 414 to provide a reward and/or notify the user application. As described herein, a reward can include virtual points or coins or can include real-world rewards (such as TV time). In the case of challenge failure, the method 400 can proceed to block 412 to notify the user application of failure.

Challenges can be weekly or a daily goal, such as entering information about food, exercise or medication intake. Examples of rewards are getting extra TV time, getting extra play time, etc. This is a way for parents to reward their children for choosing a healthy lifestyle. Once the parent sets a goal and a reward for their child, the child can get a notification on their application and has the option to accept or deny it. If they accept it, they have to meet their goal in set amount of time. Their progress can be displayed in a daily missions user interface. For example, if they enter information about exercise, it will display that progress in a daily missions report page and it will also show how much percentage of their weekly goal has been met. Users can also see a summary report of their daily, weekly, biweekly and monthly egv average values. They are also able to correlate their average egv value to their data entry. For example, they can see what their average egv was two hours before and after entering their activity information or after food or water intake. Parents can also be able to review child's health summary to then directly communicate with them about their progress. Parents can also be notified when a child accepts or denies a daily/weekly challenge and their daily and weekly progress.

As described herein, the user application can include a game. The goal of the game can be to build a Tree Town. It is a town that is shaped like a tree. There is a store that has items such as schools and houses that users can buy and place into their Tree Town. When the town (or current screen) fills up with items bought from the store, users move up to the next level, which is a new kind of a town. In order to make a purchase from the store, users need to have coins. They are assigned default coins when they sign up to the user application. In order to earn more coins, they have to complete missions which are to enter food, medication and activity data. Completing each such mission gives them an amount of coins. The purpose of the game is to increase user engagement with the user application unlike other diabetes application where there might not be an incentive to use the application. The more data they enter and the more challenges they complete, the more coins they earn and also they get better information about their health and how their lifestyle affects their health.

Figure 5:
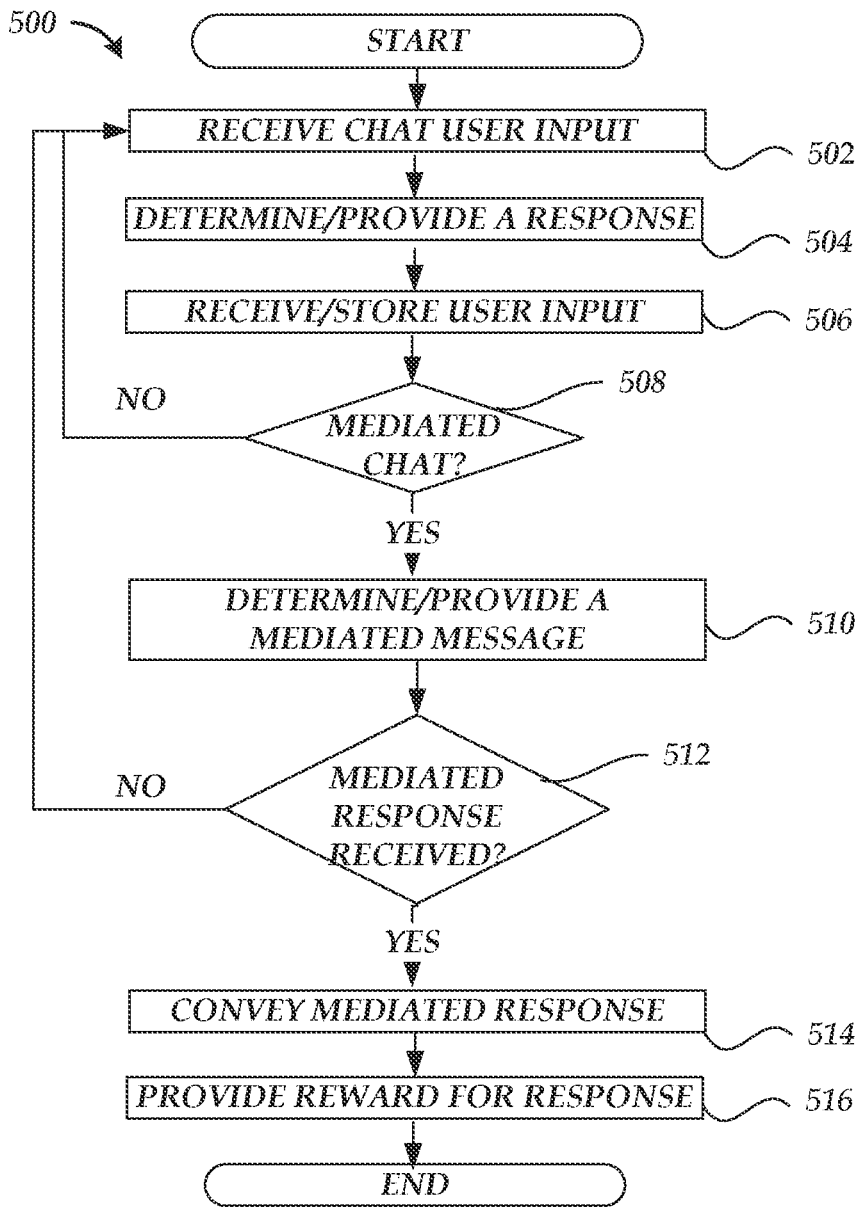
FIG. 5 is a flowchart of an example chat method, according to some embodiments of the present disclosure.

FIG. 5 is a flowchart of an example chat method 500, according to some embodiments of the present disclosure. Although the method 500 is described in conjunction with the systems of FIGS. 1A-1B, any system configured to perform the method, in any order, is within the scope of this disclosure. The method 500 may be performed by the various components of the processing and communication system 100 of FIGS. 1A-1B as discussed herein. Depending on the embodiment, the method 500 may include fewer or additional blocks and/or the blocks may be performed in an order different than is illustrated. The chat functionality in the user application can aid the user by providing a centralized place to interact with the character to get valuable feedback regarding health metrics, engage in cognitive behavioral therapies such as breathing exercises or meditation exercises, and/or learn more about how to use the user application.

At block 502, chat user input can be received. For example, the user application can receive chat user input. At block 504, a response can be determined and/or provided. In some embodiments, the user application can include chatbot logic, as described herein. In other embodiments, the system 100 can include chatbot logic, as described herein. For example, FIGS. 18, 19, 20, 21, 22, 23, 24, 25, 26, 27, and 28 are flowchart(s) of an example chatbot method. The chatbot can use a machine learning model to map user input to stored responses. At block 506, user input can be received/stored. For example, the user application can save some of the responses in the chat graphical user interface.

In some embodiments, the user application can use socket technology to emit messages from the client (the user application) to the system 100 and vice versa. Each message can be an object that can have a certain signature that can match with a corresponding action that maps to a particular process. For example, if the user requests a weekly summary of their health data through chat, a message emitted from the user application to the system 100 can contain an instruction for a weekly summary. An example message with pseudo instructions is provided below in Table 12.

TABLE 12

```
weeklySummary: {
    Messages: [
        {
        Type: 'MESSAGE',
        Instruction: 'enjoy!',
        Text: <unique code mapping
        to text within in-house library>',
        performCommand: 'goTo',
        path: 'WeeklyChart',
        }
    ]
}
```

The system 100 can look up an action in a library and if one exists, the system 100 can emit a message to the user application with properties/a message of how to proceed. In the example of Table 12, the system 100 locates an action and the action contains only one message in its Messages property. Each message can be processed by the user application and can perform an operation based on the keys within each message. Continuing with the example, the user application uses the "performCommand" and "path" as signals to redirect the user application to the weekly chart in the health summary user interfacen, and generates the response from the character (e.g., Eddii) that will be presented in the chat user interface from the text field, which is retrieved in a library in the system 100.

At block 508, it can be determined whether the chat message was a mediated conversation. For example, the chatbot logic can include a function to classify whether a message is intended to be mediated message. As described herein, a mediated conversation helps parents avoid nagging their child to perform diabetes-related tasks, such as taking insulin or checking their EGV, and helps with the parent getting the correct information from their child. The system rewards the child every time he/she responds to a question from their parent and participate in the conversation. A machine learning model can also be used to classify whether chat message is a mediated message. If the message is not for a mediated conversation, the method 500 can return to block 502 to continue receiving additional chat messages. Otherwise, the method 500 can proceed to the block 510 for determining and/or providing a mediated message to the child user application. The system 100 (and in particular the processing cluster 106 and/or the event listener 108) can mediate a message to the child user application, such as a message asking about the child user's medication, exercise, food, or analyte status.

At block 512, it can be determined whether a mediated response is received. The child user application can wait for a response to the mediated inquiry. If a response is not received (which can be for a threshold period of time), the method 500 can return to block 502 to continue receiving additional chat messages. Otherwise, the method 500 can proceed to the block 514 to convey the mediated response to the parent user application. The system 100 (and in particular the processing cluster 106 and/or the event listener 108) can convey the mediated response to the parent user application. At block 516, a reward can be provided to the profile of the child user. In particular, the system 100 can provide a reward for responding in the mediated chat conversation.

Figure 6:
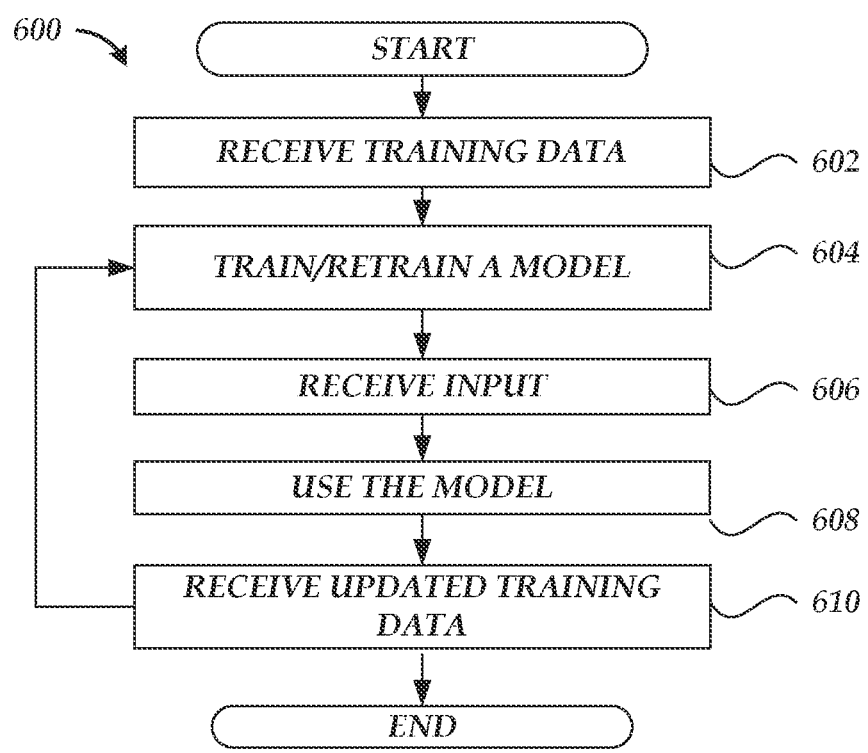
FIG. 6 is a flowchart of an example machine learning method, according to some embodiments of the present disclosure.

FIG. 6 is a flowchart of an example machine learning method 600, according to some embodiments of the present disclosure. Although the method 600 is described in conjunction with the systems of FIGS. 1A-1B, any system configured to perform the method, in any order, is within the scope of this disclosure. The method 600 may be performed by the various components of the processing and communication system 100 of FIGS. 1A-1B as discussed herein. Depending on the embodiment, the method 600 may include fewer or additional blocks and/or the blocks may be performed in an order different than is illustrated. The machine learning method 600 can be applied to various aspects of the processing and communication system 100.

At block 602, training data can be received. In the case of chatbot keyword training, the system 100 can receive questions, answers, mapping of questions to answers, and word dictionary data. The system 100 can process the training data. For example, the system 100 can vectorize the questions or dictionary data. The system can further generate labels from the questions and answers by mapping the questions to the answers. In the case of health recommendation training, the system 100 can receive analyte, mood, exercise, and food intake data. The system can also vectorize the analyte, mood, exercise, and food intake data.

At block 604, a model can be trained or retrained. For example, in the case of a chatbot context, the system 100 can train a classifier using a Naïve Bayes algorithm and by using the vector data and the labels as input. In another embodiment, the system 100 can train a convolutional neural network (CNN) using the analyte, mood, exercise, and food intake data in a vector format. In the context of a CNN or reinforcement learning generally, the system 100 can use a reward function. An example reward function can more reward activities (such as exercise and/or food intake), which can result in more improved analyte levels. Other machine learning models can be used by the system 100, either supervised or unsupervised depending on the context.

At block 606, input can be received. For example, in a chat context, the user application can receive textual input. In the case of a recommendation context, the system 100 can receive user data to generate a recommendation. At block 608, the model can be used. In some embodiments, the model can be used by the user application and/or by the system 100. For example, a chat classified model can receive the textual input and output a probability or a selected response from a group of possible responses. In another context, a recommendation machine learning model can receive user data and can output a recommendation. In some embodiments, the output recommendation could be about how much to eat, when to eat, and/or how much or when to exercise. In other embodiments, the output recommendation could be a reward amount or a selected text for encouraging a user.

At block 610, additional training data can be received. For example, the system 100 can receive updated chat text from multiple user applications. In other examples, the system 100 can receive updated user data, including updated analyte, mood, exercise, and food intake data. As shown, the method 600 can return to block 604 to retrain the model in some embodiments.

Technology for assisting users with diabetes is improving, but many users still struggle to maintain good health. Biological feedback loops are not easily replaced when conscious choice intervenes in the feedback loop. The described system uses frequent feedback from a medical device (e.g., a continuous glucose monitor or CGM) as its primary source of data input, but it employs additional algorithms, dynamic graphical user interfaces, and reward systems to encourage inputs from the user, and as a result achieve better medical outcomes. An analyte such as glucose can be monitored periodically using a continuous glucose monitor. A series of data can be analyzed to establish a current (most recently measured) level, a trend direction, a trend slope, a volatility, a confidence level, etc. The data and this related information can be transformed into psychological, emotional, or other human-experience cues that are conveyed to a user. The human experience cues can also be translated in the reverse, allowing a user to input a mood, a physical description, lifestyle choice or health information that is automatically transformed into a control input having technical significance for adjusting an analyte (e.g., glucose) and other substances that affect analyte levels (e.g., insulin).

A continuous analyte monitor ideally provides a reliable stream of accurate data points. In this context, multi-factor control algorithms, translation protocols, dynamic graphical user interfaces, and reward systems are useful to allow such an already-accurate and reliable analyte monitor to be used for better medical outcomes. FIGS. 7 and 8 summarize some aspects of relevant factors and interface elements.

FIG. 7 shows part of a table summarizing levels and indicators. Blood glucose (BG) level can be represented by three letters: R=Blood glucose "In Range"; L=Blood glucose "Low"; and H=Blood glucose "High." R can correspond, for example, to 70-150 mg/DL, L can indicate below 70 mg/DL, and H can indicate over 150 mg/DL. Alternatively the target range can be within 80-100 mg/DL, or another appropriate sub-range. The levels can also be associated with colors. For example, a first color (corresponding to the "R" icons), such as green, can indicate the status quo is desirable. A second color (corresponding to the "H"

icons), such as yellow, can indicate caution, and a third color (corresponding to the "L" icons), such as red, can indicate danger or the need to take action. Icons associated with these letters can also indicate a trend with a point extending from the letter. A point extending directly up can show analyte level is rising relatively rapidly (e.g., for glucose, 2-3 mg/dL per minute, or up to 45 mg/dL in 15 minutes). A point extending directly down can show that an analyte level is dropping relatively rapidly (e.g., for glucose, 2-3 mg/dL per minute, or up to 45 mg/dL in 15 minutes). If a point includes additional color or a separate graphical appearance, this can provide additional trend information. For example, a point extending up or down that is also filled with a color (e.g., red, green, or yellow) can indicate an even more extreme slope of the trend (e.g., for glucose, more than 3 mg/dL per minute, or more than 45 mg/dL in 15 minutes). Points extending directly to the right can indicate the trend is generally stable—neither increasing nor decreasing recently (e.g., changing by less than 1 mg/dL/minute, up to 15 mg/dL in 15 minutes). Points extending up and to the right can indicate a rising trending, but not rising as quickly as a point extending directly up (e.g., for glucose, 1-2 mg/dL per minute, or up to 30 mg/dL in 15 minutes). A point extending down and to the right can indicate a gently declining trend (e.g., for glucose, 1-2 mg/dL per minute, or up to 30 mg/dL in 15 minutes).

Referring further to FIG. 7, in the row for level 1, a medical condition can be good with relatively stable analyte levels, as indicated by the "R" icon in the first color (such as green). In the row for level 2, analyte levels can be slightly declining, or slightly climbing. In this case the user must be aware but need not be too worried as analyte levels are still within range. In the row for level 3, a user can be on the right track but slightly outside (either low or high) of the ideal range for analyte (e.g., glucose) levels. This can be the case if the slope or trend of the data is toward the good "R" range.

In the row for level 4, the data can suggest that the user should start to worry and pay attention to the trend. This row is bifurcated into a blood glucose high section at the left, and a blood glucose low section at the right. A user compliance protocol can help a user understand the significance of these levels by associating a graphical character's state, weather, environment and other factors with these conditions. For example, high glucose can be associated with drought, desert, hot sunshine, and thirst. In contrast, low glucose can be associated with water, rain, flooding or freezing temperatures.

In the row for level 5, the data can suggest the user should be worried since both the analyte level and trend need correction.

In FIG. 8, further levels are indicated with a similar format to that provided in FIG. 7. The row indicating "Danger Level 1" corresponds to blood glucose that is too high (e.g., 150-400 mg/dL) and trending upwards, or blood glucose that is too low (e.g., 40-75 mg/dL) and trending downward. The row indicating "Danger Level 2" corresponds to blood glucose that is much too high (e.g., above 250 mg/dL) and trending up, or glucose that is much too low (e.g., below 50 mg/dL), the most dangerous zone for blood glucose levels, and trending down.

However, as can be seen from the various permutations of these indicators, it may be difficult for a user to keep track of the nuances and differences between these various symbols—and what they mean for the user's health. It is therefore useful to present an improved graphical user interface to allow user to mentally and emotionally engage with a character that can demonstrate these nuances in a relatable way, and to convey additional clues about the current status and what actions are warranted to improve it. This can improve a user's ability to appreciate the danger, the lack of danger, etc., and to do so more quickly, in a fun and engaging way. It can also cause a user to care more, especially if a character or personality depiction is employed as a surrogate for the health or well-being of the user herself or himself.

More generally, existing systems include graphical user interfaces that exclusively present glucose data with numerical indicators and/or graph charts. Much like the permutations of indicators described above, the existing graphical user interfaces often fail to convey meaningful information to a user in an efficient manner. For example, many users have difficulty comprehending math-related concepts and the exclusive use of numerical indicators and/or graph charts in a graphical user interface can be confusing to such users.

Various embodiments of the present disclosure provide improvements to various technologies and technological fields, and practical applications of various technological features and advancements. For example, as described above, some existing systems are limited in various ways, and various embodiments of the present disclosure provide significant improvements over such systems, and practical applications of such improvements. For example, embodiments of the present disclosure can present improved graphical user interfaces with visual metaphors such as, but not limited to, weather, color, temperature, foliage, climate, and/or character mood, that can rapidly convey meaningful information to some users. Thus, the systems and techniques described herein can result in improvements to graphical user interfaces. Moreover, detected physiological data of a user can be recorded and processed by rules of the system that can cause the improved graphical user interface to dynamically update as described herein. Thus, various embodiments of the present disclosure can be inextricably tied to, and provide practical applications of, computer technology.

Figure 10:
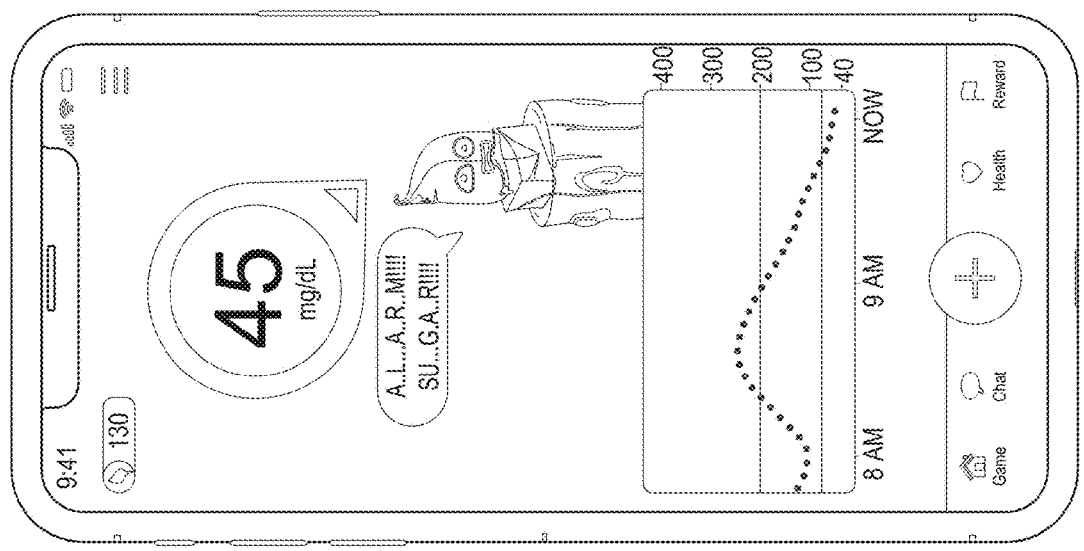
FIGS. 9, 10, 11, 12, 13, 14, 15, 16, and 17 depict example graphical user interfaces, according to some embodiments of the present disclosure.
Figure 9:
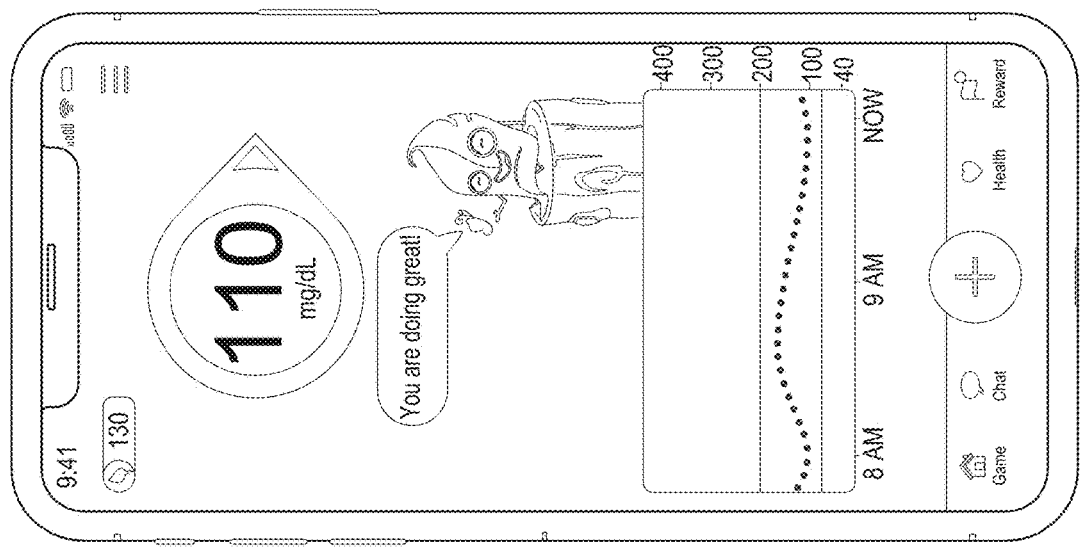
Figure 11:
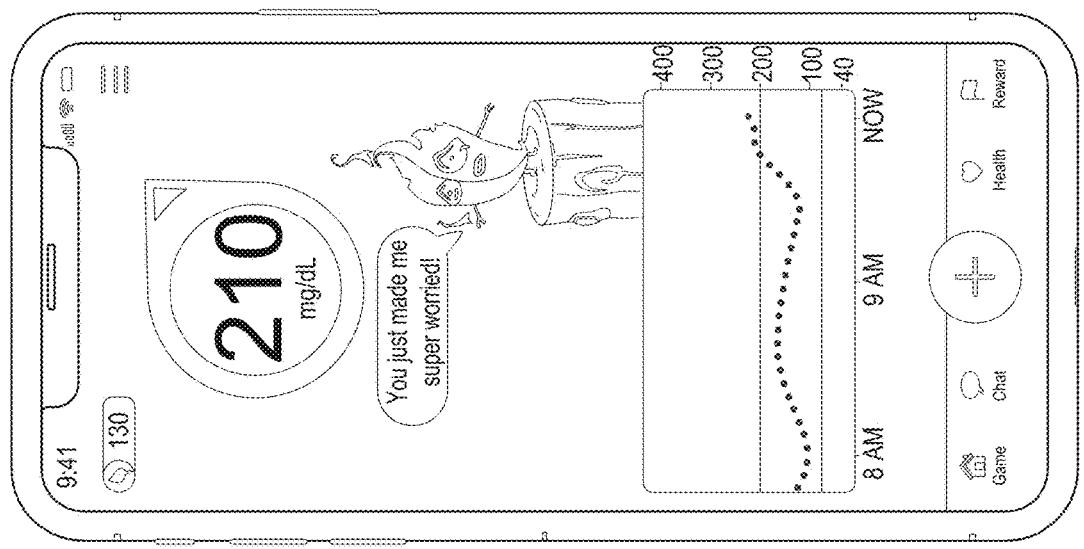

Factors that can be employed to elicit action from a user (in addition to the data indicators described and categorized above), include illustrations of: weather, color, temperature, foliage, climate, and/or character mood (e.g., happiness, sadness, desperation, contentment, satisfied relaxation, urgent frenzy, etc.). Color, brightness, and animated character movement on a user's screen can be especially useful to catch their attention (if needed) and motivate action. FIGS. 9-11 provide examples of how various factors can together accomplish these goals of feedback and motivation to a user.

Example embodiments can address and/or affect user behavior with virtual objects, virtual environments, and automated virtual protocols. Thus, described systems can reward the user for physical, emotional, lifestyle and medical inputs, engaging the user on multiple levels to generate, in combination with data garnered from the continuous glucose monitor, a reliable and personalized feedback system for the user.

FIG. 9 shows a graphical character (Eddii) relaxing contentedly on a tree branch, with one or more colors (e.g., the color green) that are associated with being in a "good" condition. This corresponds to a stable glucose level of 110 mg/dL, within a healthy range. This also corresponds to the middle "R" in the top row of FIG. 7 in the first color and allows a user at a glance to become aware of the present health and glucose status.

FIG. 10 shows that the graphical character is freezing cold in an ice cube with a blue icy background in response to low blood glucose (45 mg/dL) that is trending low. This also corresponds to dangerously low levels of glucose and the need for immediate action by the user.

FIG. 11 shows the graphical character burning with smoke appearing in response to high blood glucose of 250 mg/dL and trending up. The background is turned smoky and brown. This also corresponds to dangerously high levels of blood glucose.

Additional visual graphics can help educate or remind a user about a current status, history, or future status. For example, a third dimension can be employed to show how the graphical character's mood or demeanor or position has changed over time. A graphical character can be depicted as progressing through different landscapes or biomes—a desert representing low glucose, and a rain forest or arctic landscape representing too much glucose, for example. The graphical character's journey can be depicted in two dimensions (like a game piece in monopoly progresses between different locations) to help a user see where the graphical character has been and where he will go if a trend continues. The graphical character's journey can also be depicted in three dimensions with the background (near the vanishing point in a perspective drawing) representing past, or future, depending on which way the character is shown to be traveling through the virtual world. Thus, many aspects of three-dimension computer gaming can be employed for a graphical character such as Eddii and the virtual environment for this graphical character. The system can further reinforce the message from these figures by sending a user texts, calling the user, attempting to chat with a user, etc. Thus, the character described herein can also embody or represent a "chatbot" or other interactive entity. From time to time, a user may elect to change characters, change modes, or change color schemes in order to maintain interest and motivation for healthier outcomes.

Figure 17:
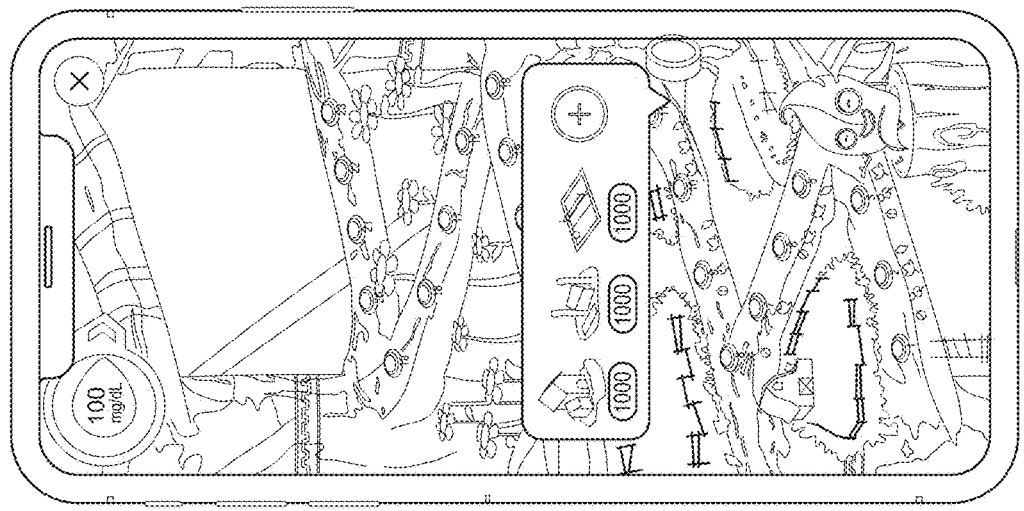
Figure 18:
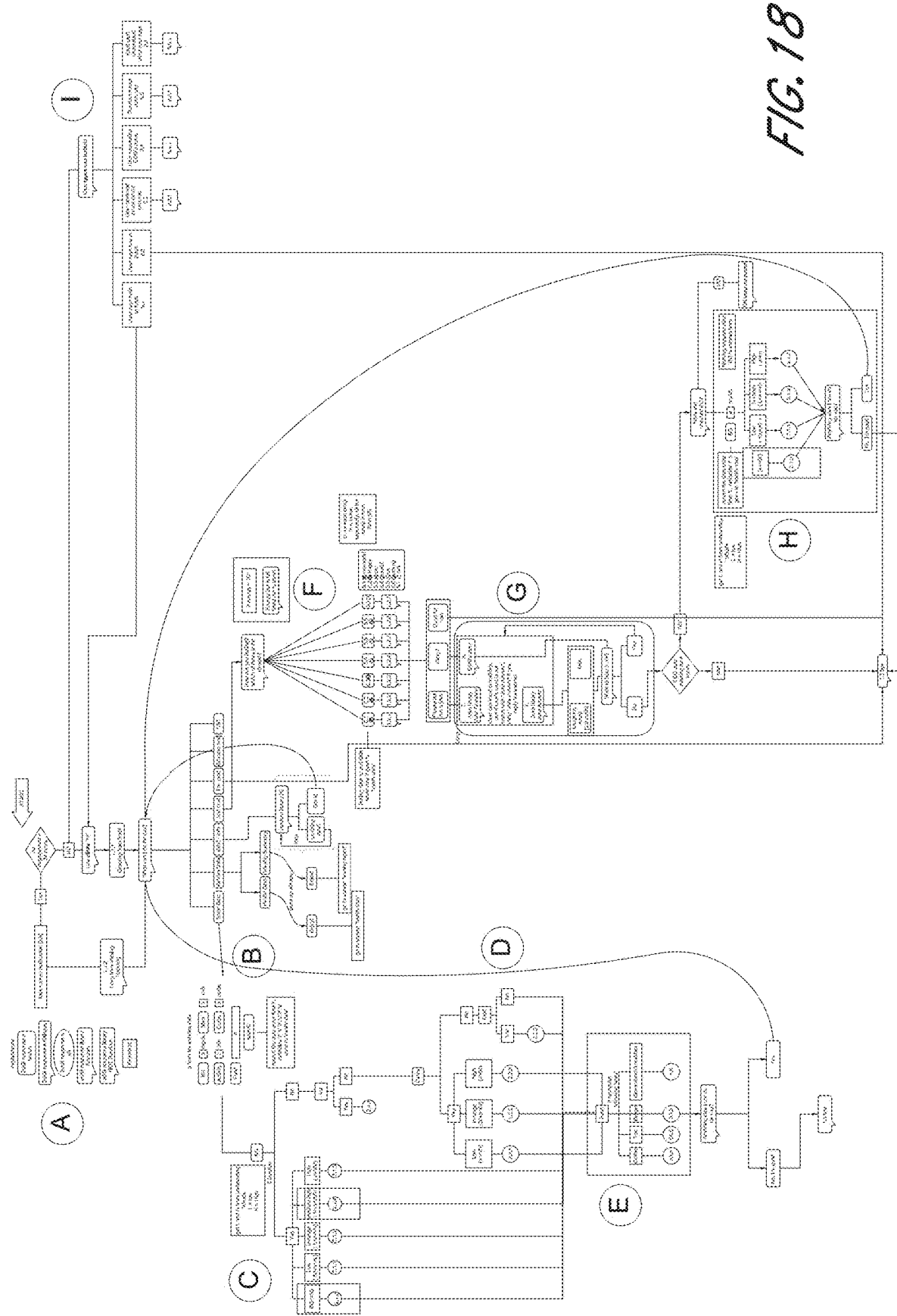
FIGS. 18, 19, 20, 21, 22, 23, 24, 25, 26, 27, and 28 are flowchart(s) of an example chatbot method, according to some embodiments of the present disclosure.

The user is rewarded for lifestyle, emotional, physical and medical data entry through a gamified system, whereby the user can collect both short-term and long-term in-app rewards. For example, FIG. 17 shows a user building a tree town, with the option to purchase a house, bench and tennis court for their virtual town with coins earned by entering data into the app. The user can also unlock new locations after sufficient data entries and access new collectibles. For long-term rewards, for example, users can win a new character friend or additional items for five insulin entries per day, or entering feelings for three days in a row and practicing behavioral therapy through chatbot functionality.

The user can also be rewarded for the time their glucose level was maintained within range, such that rewards are directly related to their glucose levels. For example, a user who maintains their glucose levels within range 65% of the day can be rewarded with both virtual (in-app) and real-life rewards.

The user can opt to share their substantially real-time blood glucose and summary health information with a relative or a close acquaintance, such as their parent(s). The character can provide the user with a real-life reward system whereby a user's relative or close acquaintance, such as a child's parent, can set periodic health goals for their child, and if achieved, the child will receive a real-life reward set by the parent, such as extra TV time or a bike. For example, a parent can set a goal of entering meals three time a day over two consecutive days for their child, and if achieved, the child will receive a real-life reward.

Figure 12:
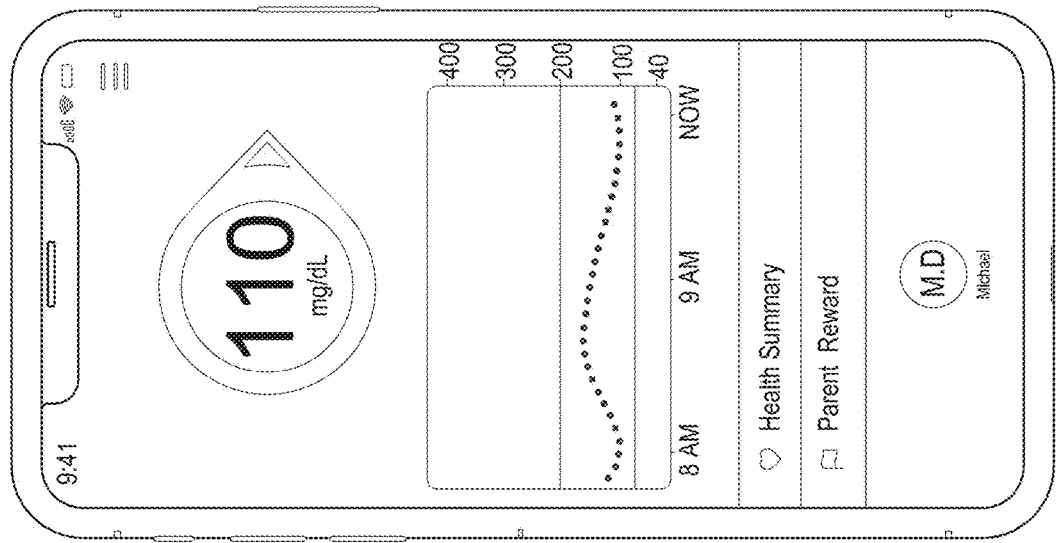

FIGS. 12 and 13 show additional graphical user interfaces, which can be part of a parent-child reward system and/or presented in an application accessible by a parent. The parent can set a goal for their child using the graphical user interface and choose an associated reward with that goal. The parent can be notified once the child has accepted the challenge.

Figure 14:
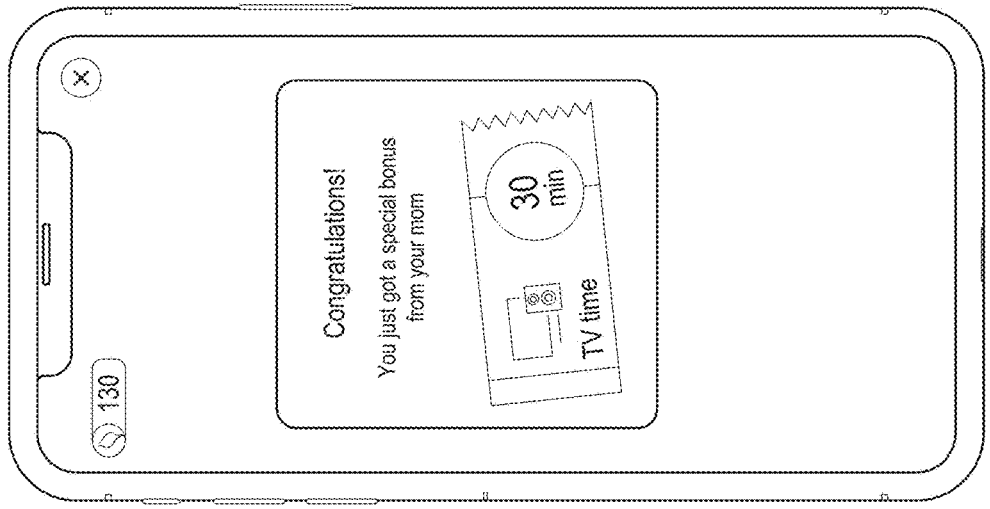
Figure 14:
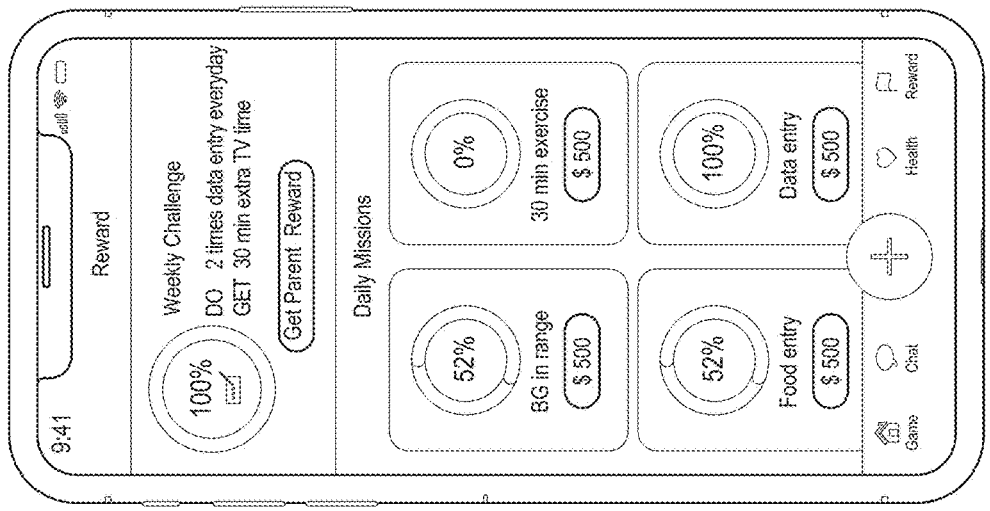
Figure 14:
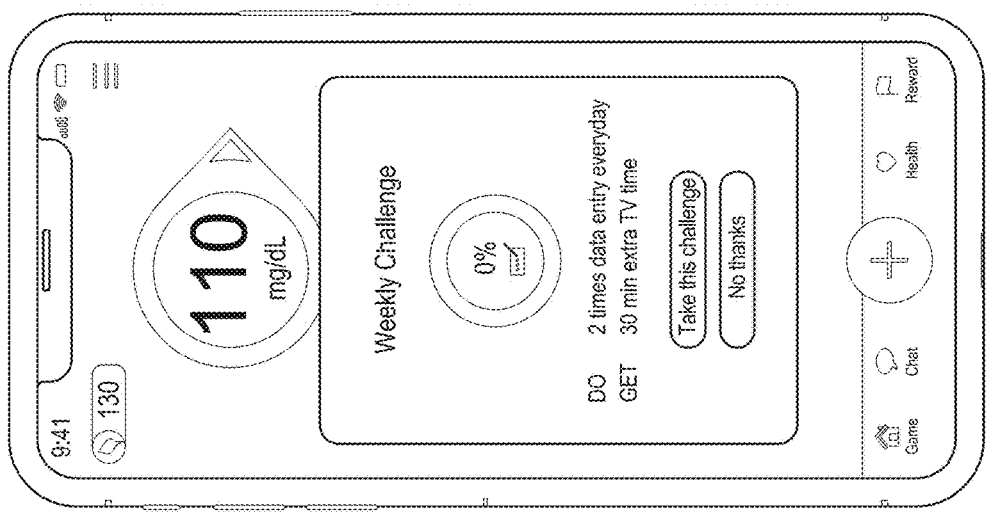

FIG. 14 shows additional graphical user interfaces, where the child can accept the challenge set by parent, and the challenge is added to the child's mission page. Ultimately, the child can be rewarded once their goal is reached.

The system can combine data obtained through gamification and various animations and aggregate it with continuous glucose data incoming from the continuous glucose monitor, creating a robust system for health pattern recognition, providing AI-enabled assistance to the user in the form of alerts, predictive analytics, and health recommendations.

One example implementation of a system is described here. The example system described herein can be independent of integration with periodic inputs from an analyte monitor (e.g., continuous glucose monitoring data). A health application can be designed to engage the user through a buddy system. A virtual character can "live" inside the application and can become the user's health buddy. The character can engage the user on multiple levels through conversation, rewards, and pattern recognition to facilitate healthy behavior and medication adherence.

The virtual character can help the user to record their health data and develop healthy habits. The application can engage users living with diabetes and other chronic conditions to track their health. Some of the character's and/or the application's features can include:

1. A virtual buddy that reacts to substantially real-time continuous glucose monitoring data and provides health cues to the user.
2. In-app reward system through games that engages the user to enter and track their health data and that allows the user to build a virtual tree town and share it with friends on social media.
3. A parent-child reward system that allows the parent to set health-related tasks and real-life rewards for their child.
4. A chatbot that offers behavioral therapy, stories, jokes and comforting and motivational quotes to the user.
5. Weekly health report that highlights health patterns and gives helpful tips.
6. Integrations with other health apps and devices, including continuous glucose monitors.
7. A graphical user interface for parents and close acquaintances to the user that allows others to track the user's health, and set periodic goals and associated rewards.

When the user opens the application, the homepage can present the user's substantially real-time blood glucose number and trend, a chart depicting historical values, and the character reacting through animations and speech bubbles to current blood glucose level(s) and trend(s). The user can earn points by chatting with the virtual character and entering health data. Extra points are awarded for healthy data entry, such as eating a healthy meal or exercising. With earned points, the user can purchase in-app items for a virtual tree town. Users can see a summary of their health data and identified patterns.

Figure 15:
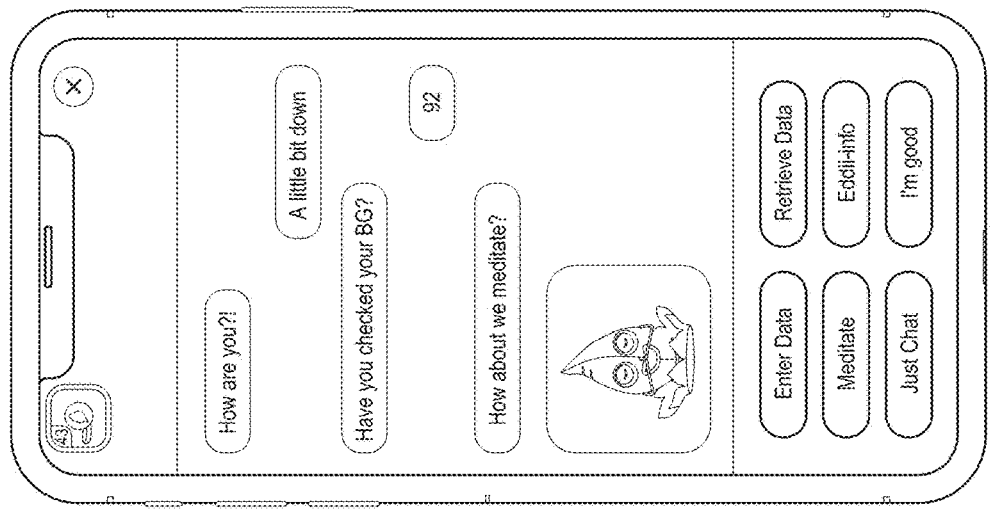

FIG. 15 shows an example chat conversation. The virtual character can be available for chat at any time, which can offer artificial-intelligence (or AI)-enabled behavioral therapy.

Various health metrics can be measured through the application. Six examples of such metrics include: blood glucose (BG), activity, medication, carbohydrates, meals and user's feelings. Once captured, these metrics can be presented on one or more types of charts. A first type is a daily chart. A user can see their daily blood glucose trend, carbs, activities, and medications. In the case of activities, the described system or platform can be integrated with a health application (e.g., Google Fit, Apple Health, etc.) for seamless data entry. A user can enter carbohydrates and medications manually, for example. A second type is a weekly summary A user's data can be summarized weekly and provided to the user. The weekly report can present health patterns that highlight the user's average blood glucose for that week, and their average blood glucose when conducting exercise and after meals. It also measures a user's blood glucose based on the user's feelings, for example average blood glucose every time the user feels tired.

Figure 16:
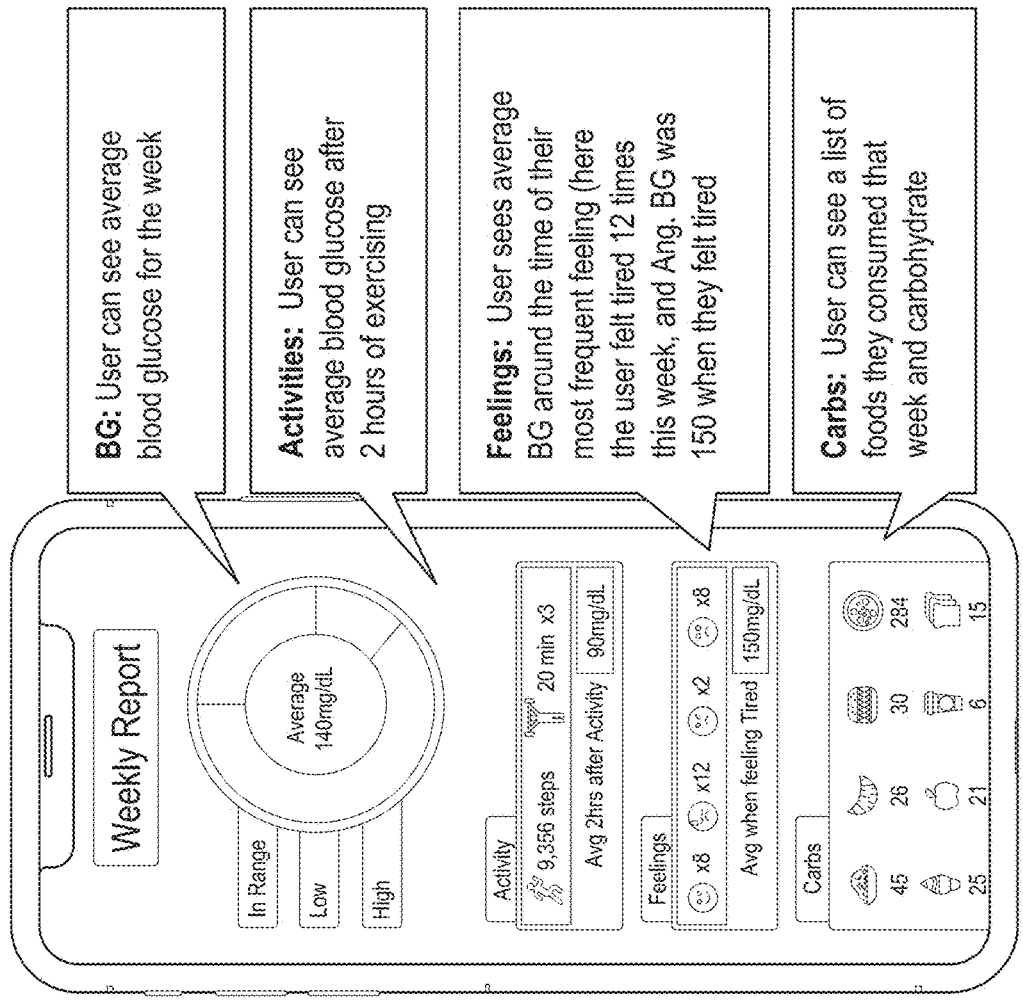

FIG. 16 shows an example weekly report.

FIG. 17 again shows an example of a game interface that can engage a user and provide "collectibles" within the application. When the user opens the data entry form, they can earn coins for every data entry. The coins can be used to purchase buildings and other items for a virtual tree town.

The character can include a chatbot that can have conversations with the user. For example:
1. The character can ask the user how they are feeling. If the user is not feeling well then the character can teach the user via cognitive behavioral therapy techniques.
2. The character can tell the user stories.
3. The character can tell the user jokes.
4. The character can celebrate with the user when healthy data is entered.
5. The character can comfort the user when health data is not great.

As described herein, the character can be a virtual diabetes health buddy. The system can employ games and software-enabled chat, with the character as a vehicle for communication. Games can reward users for healthy behavior. Users can chat with a virtual friend who understands their lifestyle and health needs and can assist with behavioral therapy. By asking questions, engaging the mind and emotions of a user more effectively, and recognizing patterns, such a system can identify more and improved health patterns.

Figure 19:
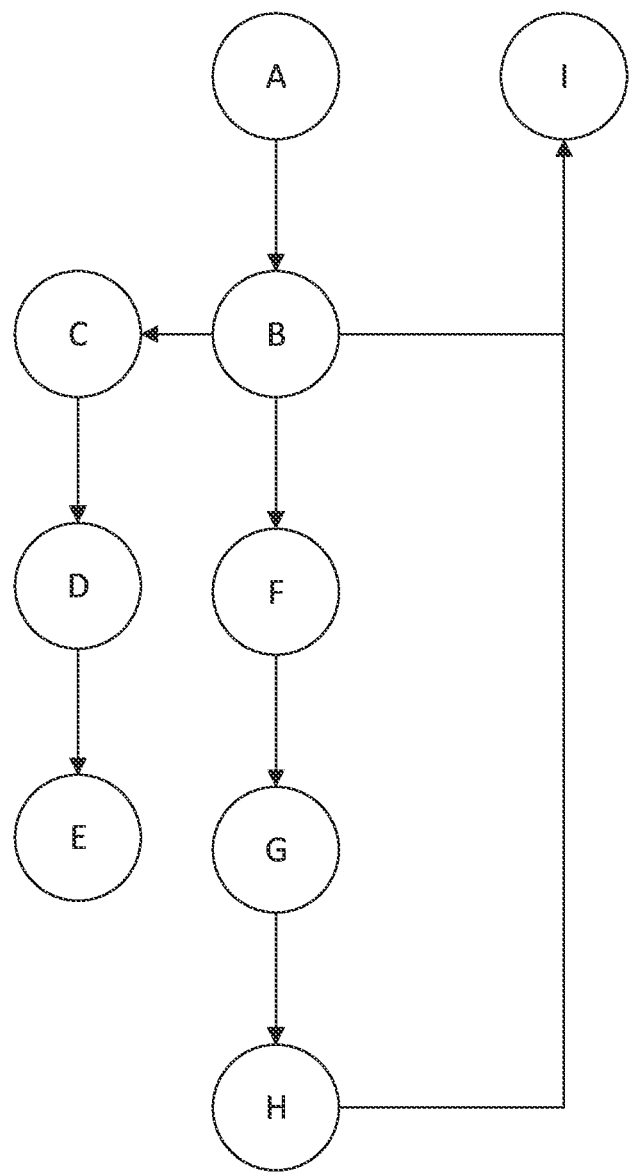
Figure 20:
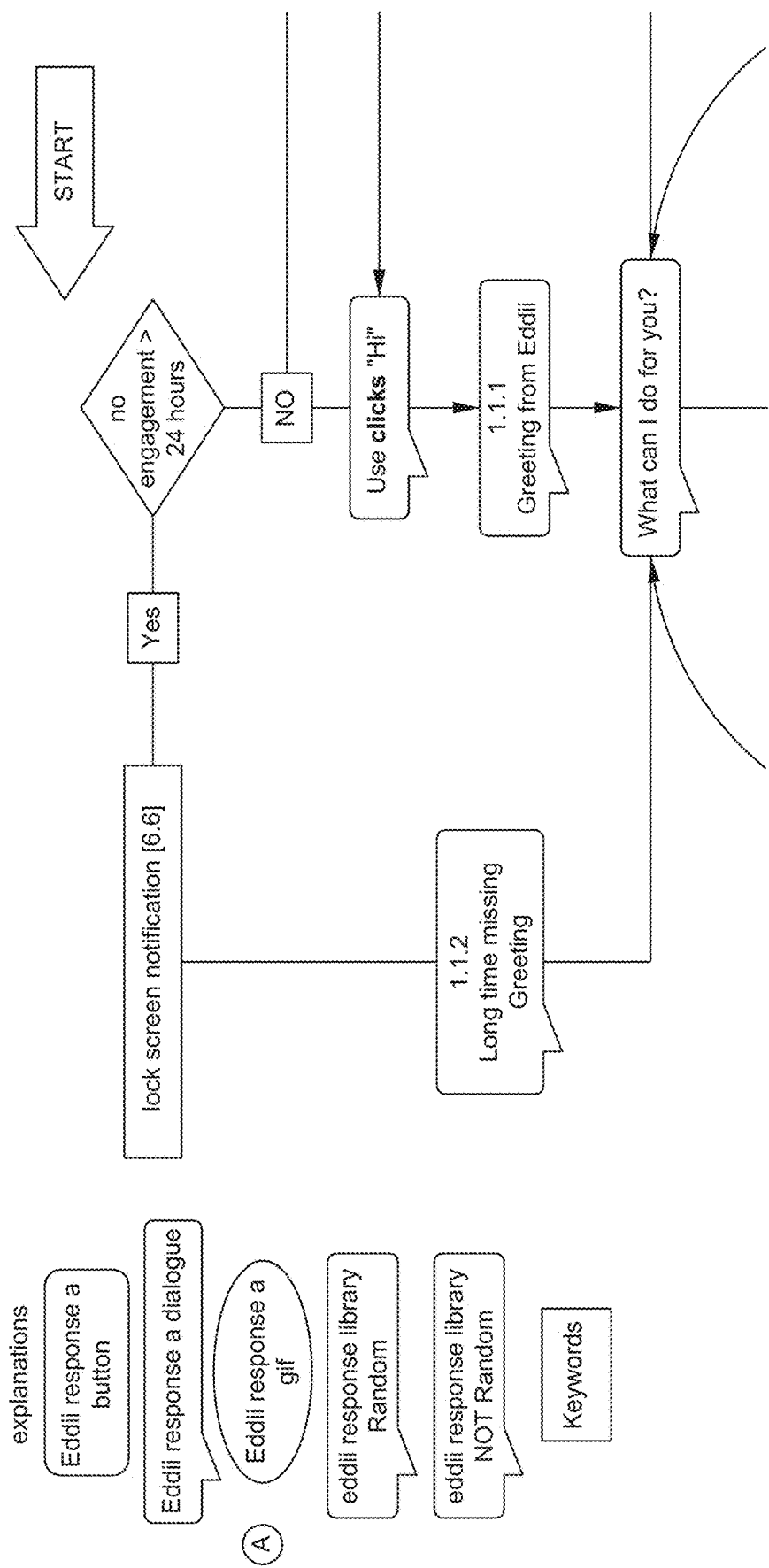
Figure 21:
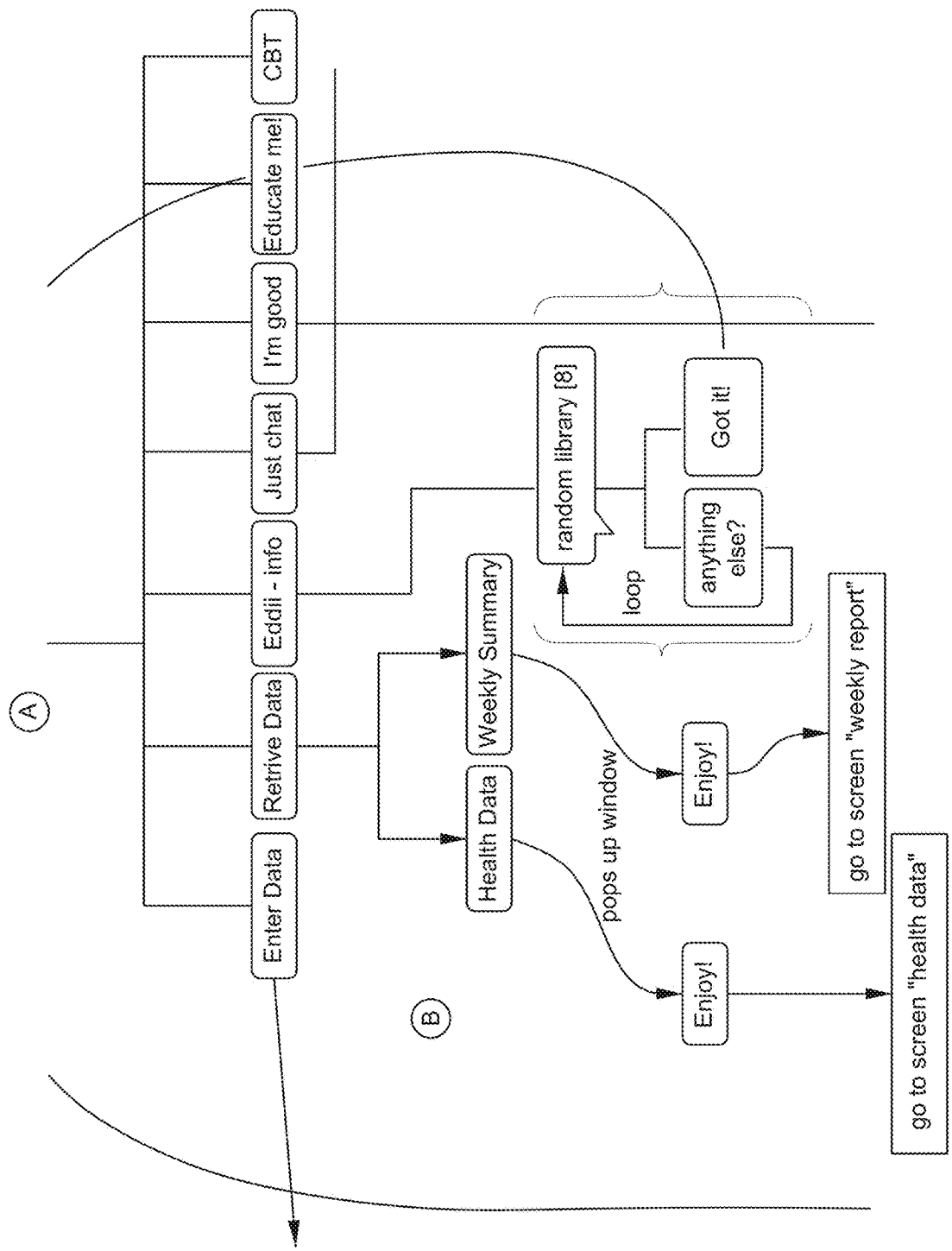
Figure 22:
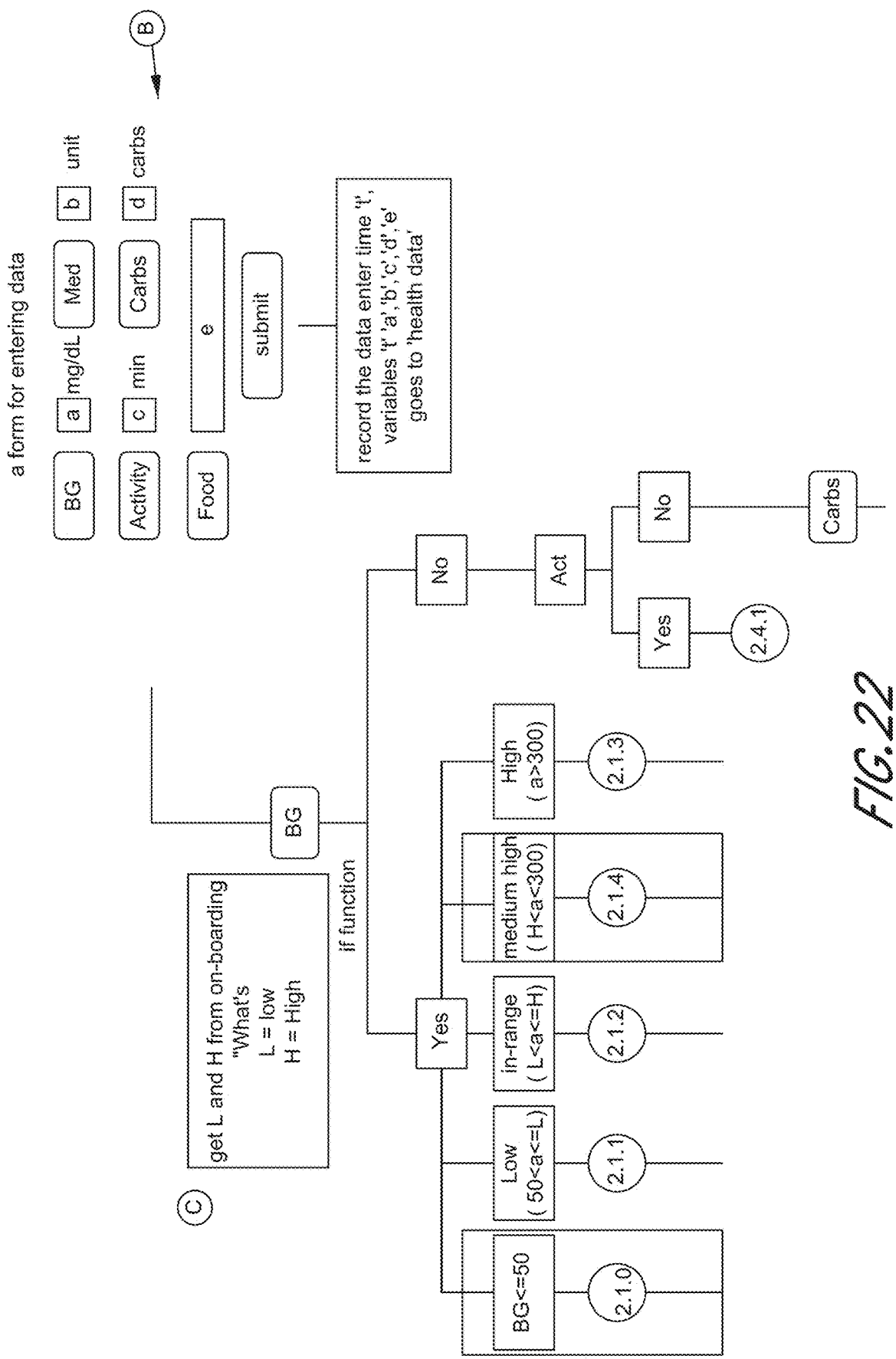
Figure 23:
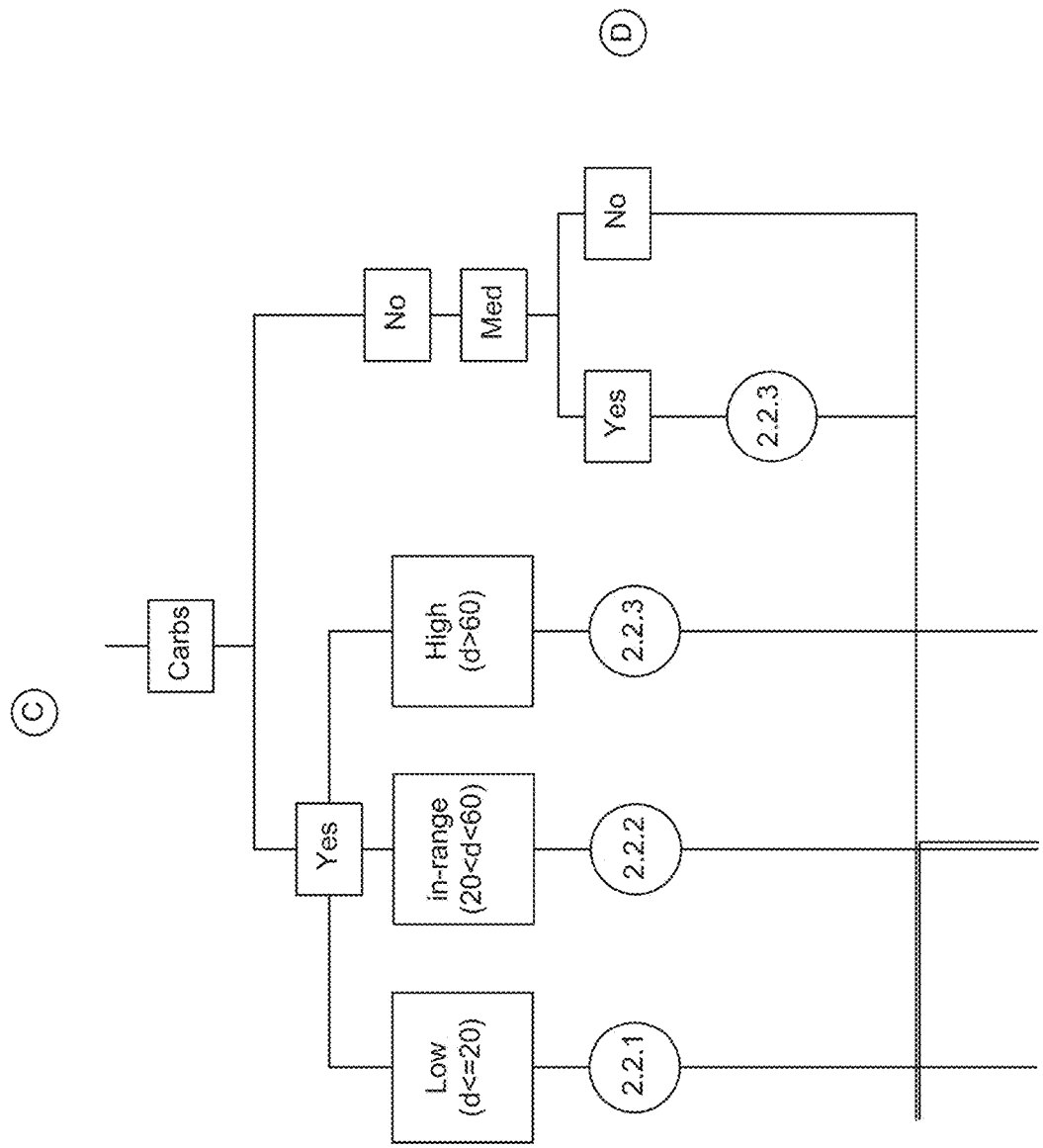
Figure 24:
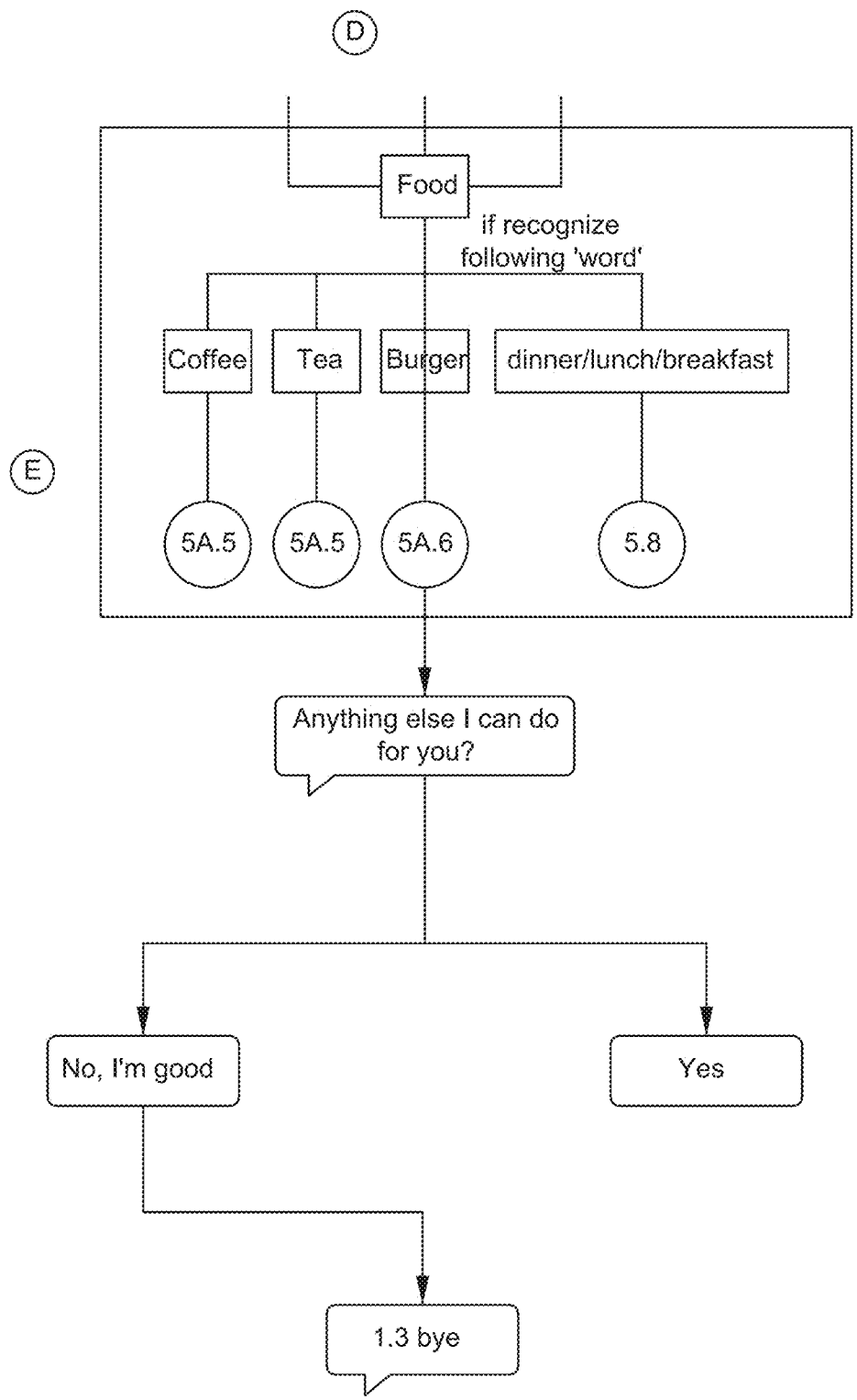
Figure 25:
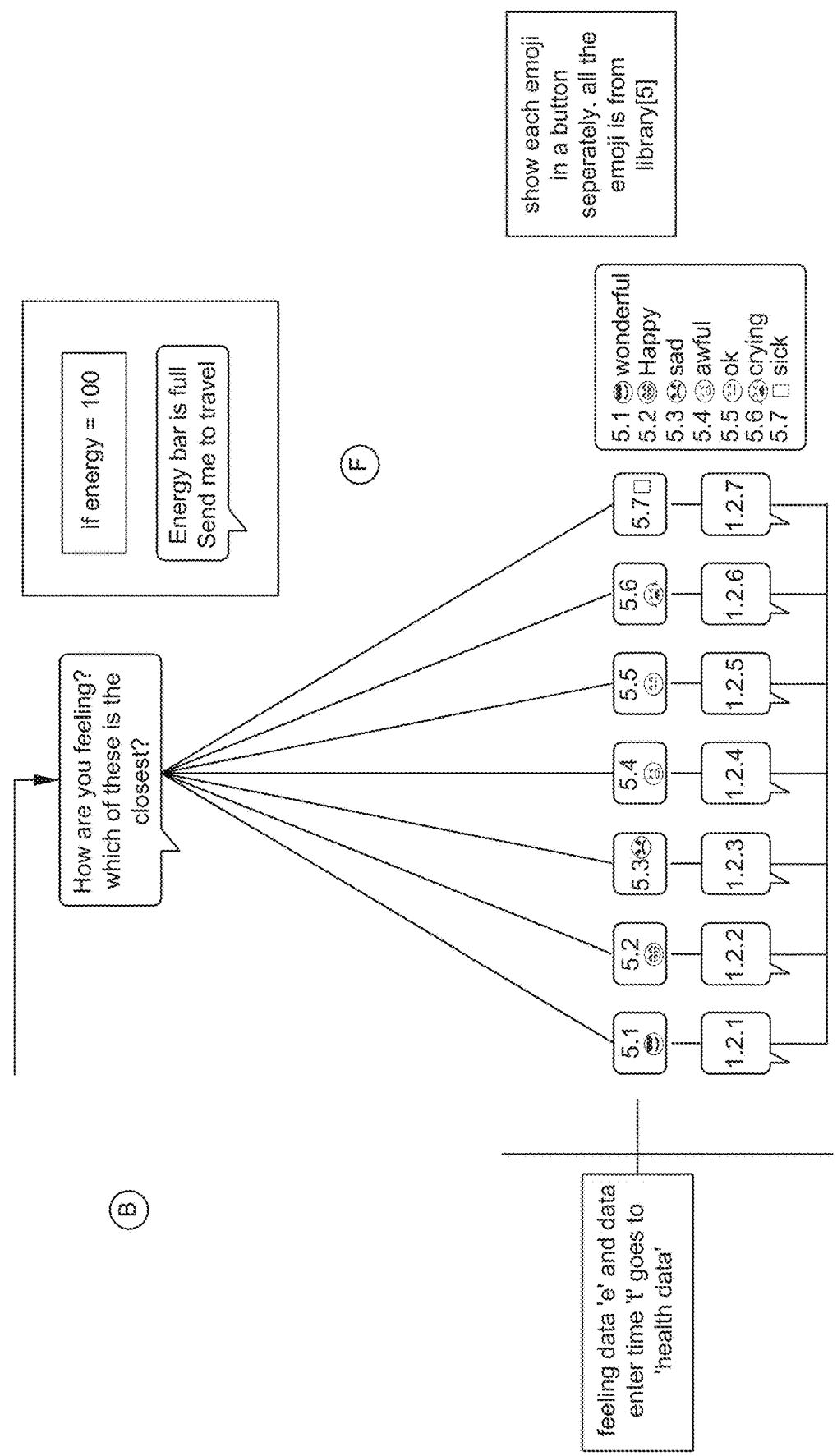
Figure 26:
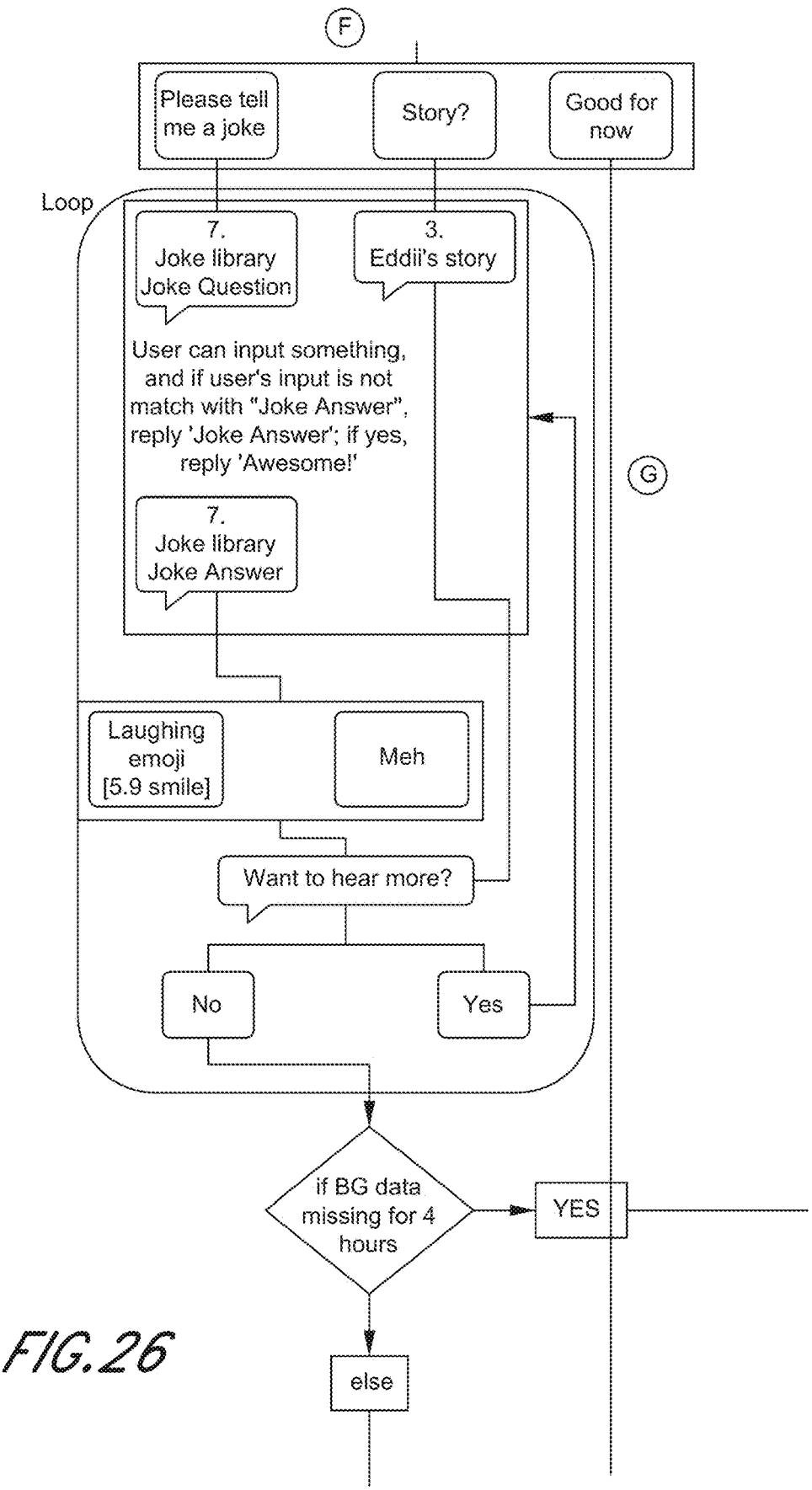
Figure 27:
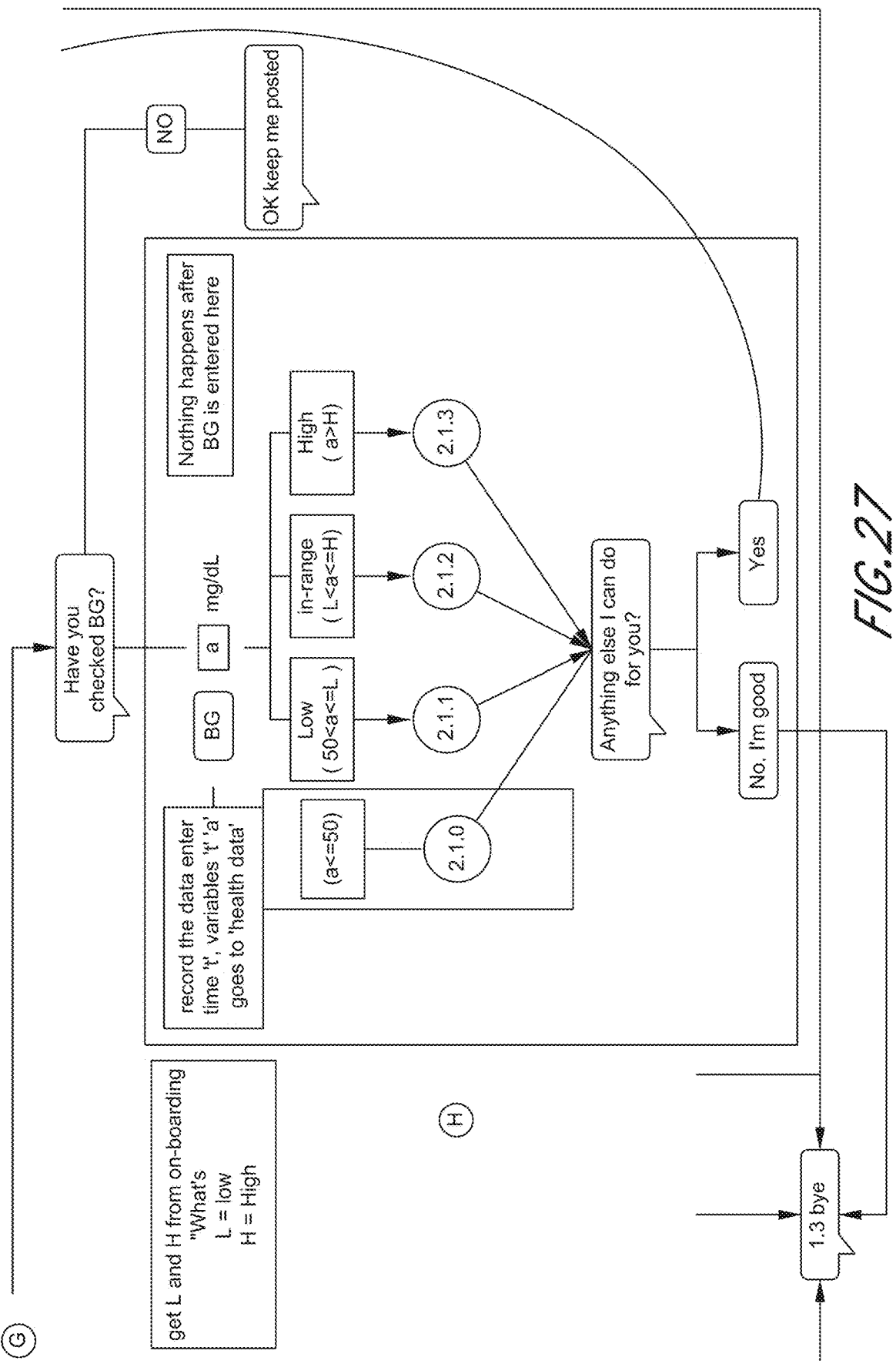
Figure 28:
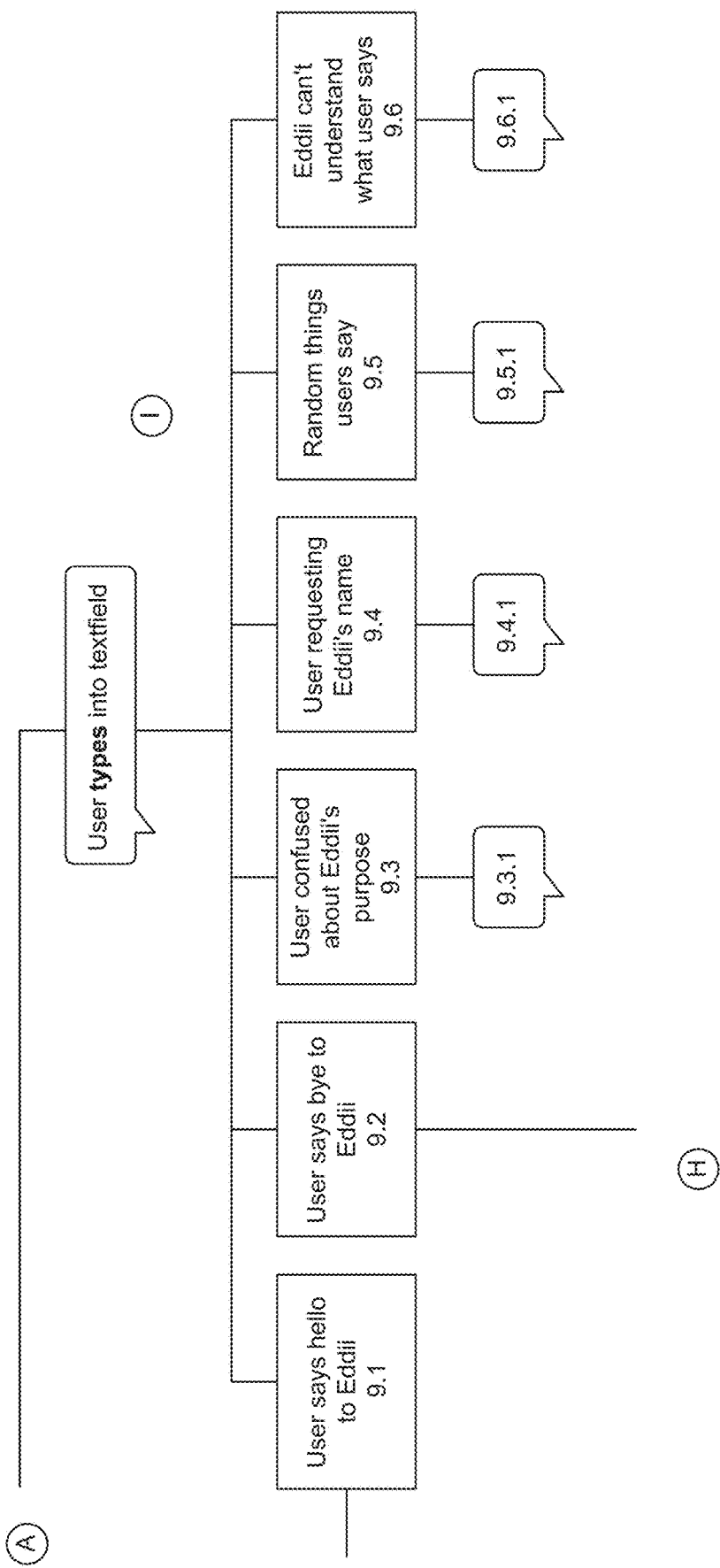

FIGS. 18-28 show a chatbot flowchart. FIG. 12 provides a high level view of the flowchart. FIG. 19 provides a generalized illustration of how the various subsections are related. FIG. 20 provides a close-up view of subsection A of the flowchart of FIG. 18. FIG. 21 provides a close-up view of subsection B of the flowchart of FIG. 18. FIG. 22 provides a close-up view of subsection C of the flowchart of FIG. 18. FIG. 23 provides a close-up view of subsection D of the flowchart of FIG. 18. FIG. 24 provides a close-up view of subsection E of the flowchart of FIG. 18. FIG. 25 provides a close-up view of subsection F of the flowchart of FIG. 18. FIG. 26 provides a close-up view of subsection G of the flowchart of FIG. 18. FIG. 27 provides a close-up view of subsection H of the logic tree of FIG. 18. FIG. 28 provides a close-up view of subsection I of the flowchart of FIG. 18.

In FIGS. 18-28, a chatbot library can be used. The library can help a system such as those described herein provide automated behavioral therapy through device interfaces in response to analyte measurements (e.g., high blood glucose) from a user. A translation glossary or correlation table in the library can help translate colloquial or individualized chat questions, terminology, jargon, questions, answers, etc. and associate them with technical medical counterparts, with electronic signals, with biological signals, and/or messages to be sent or received by one or more aspects of the system or a system user.

Chat logic and libraries can not only directly communicate with the user, but can also be used to mediate conversations between users and their relatives or close acquaintances, such as their parents, when discussing matters related to the user's health. The user's parent(s), for example, can ask the character to check on their child and ask what they are having for lunch, or how much insulin was taken by the user, without contacting the user directly. The character can then ask the user and reward them for their answer, meanwhile providing a response to the parent.

Figure 29:
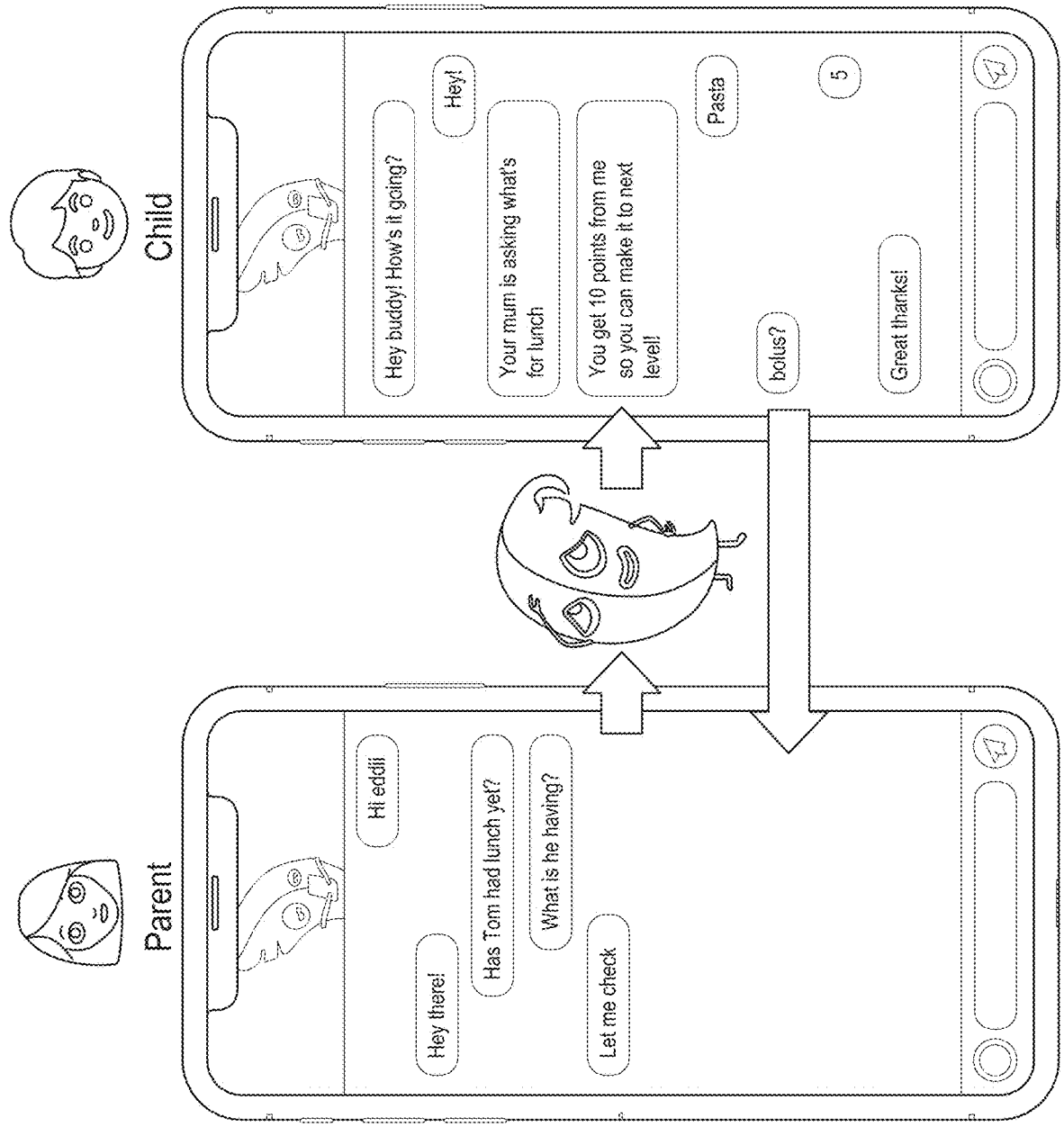
FIG. 29 depicts additional example graphical user interfaces, according to some embodiments of the present disclosure.

FIG. 29 provides an example of a conversation mediated by the chatbot between a parent and a child.

Logic and libraries such as those of FIGS. 18-28 and described herein can provide a framework for interacting with users and enhancing the artificial intelligence capabilities of the system. For example, the system may learn the vocabulary and habits of a particular user, store data that records what it has learned, and therefore more quickly interpret inputs from the user to more efficiently recommend action to improve an analyte level. For example, a user who chats with the character and uses the term "tired" within a certain amount of time of another CGM data input may benefit from a recommendation by the character to eat a favorite snack. Moreover, a reported mood shift or other clue from chat functionality may provide an independent (or, combined with continuous glucose monitoring data, a correlating) data point. Such data points can preview future measurements or actions to recommend. Thus, personalized, refined preemptive recommendations can be developed and/or delivered through the described platform. The described system, combined with artificial intelligence, can also allow aggregated ("big data") conclusions that hold true for a large percentage of individual users.

Additional Implementation Details

Figure 30:
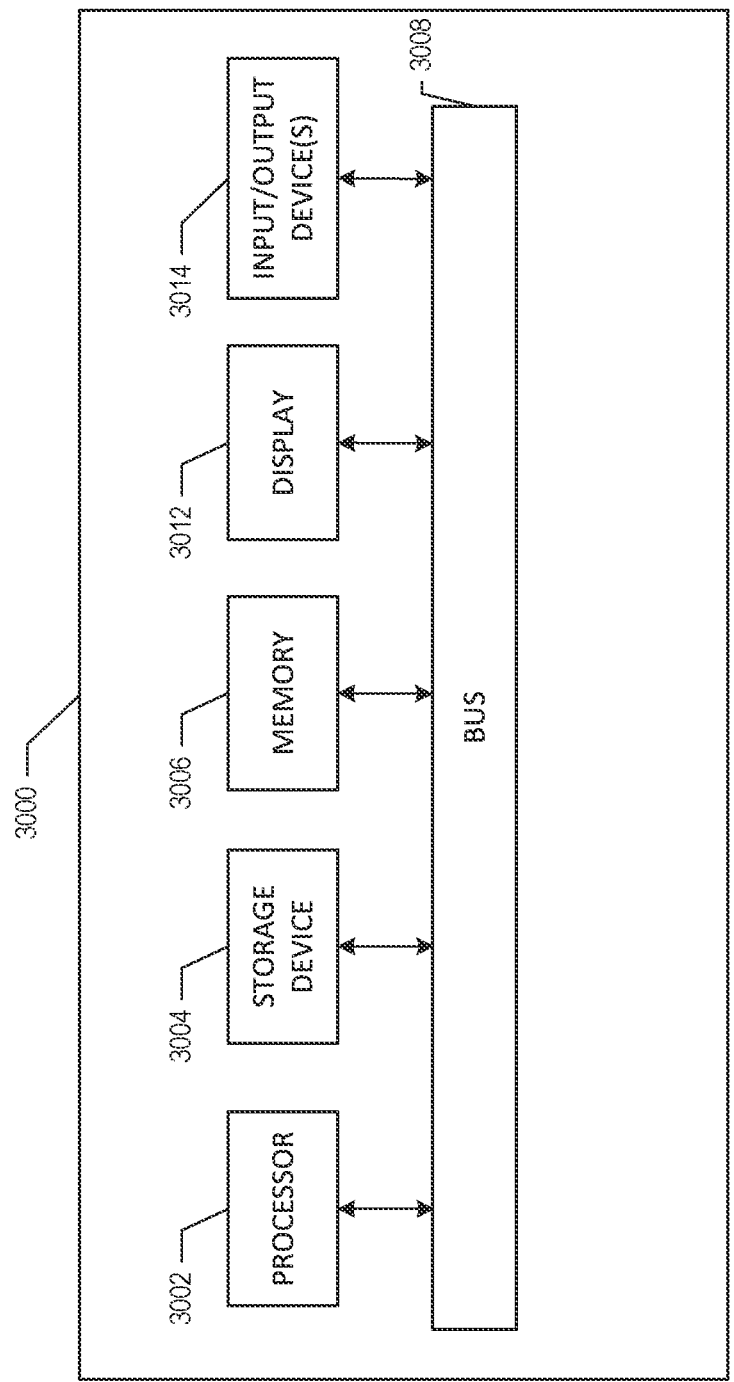
FIG. 30 illustrates an example computing system with which some embodiments of the present disclosure may be implemented.

FIG. 30 is a block diagram that illustrates example components of a computing device 3000. The computing device 3000 can implement aspects of the present disclosure, and, in particular, aspects of the processing and monitoring system 100. The computing device 3000 can communicate with other computing devices.

The computing device 3000 can include a hardware processor 3002, a data storage device 3004, a memory device 3006, a bus 3008, a display 3012, and one or more input/output devices 3014. A processor 3002 can also be implemented as a combination of computing devices, e.g., a combination of a digital signal processor and a microprocessor, a plurality of microprocessors, one or more microprocessors in conjunction with a digital signal processor, or any other such configuration. The processor 3002 can be configured, among other things, to process data, execute instructions to perform one or more functions, such as process one or more physiological signals to obtain one or measurements, as described herein. The data storage device 3004 can include a magnetic disk, optical disk, or flash drive, etc., and is provided and coupled to the bus 3008 for storing information and instructions. The memory 3006 can include one or more memory devices that store data, including without limitation, random access memory (RAM) and read-only memory (ROM). The computing device 3000 may be coupled via the bus 3008 to a display 3012, such as a LCD display or touch screen, for displaying information to a user, such as a clinician. The computing device 3000 may be coupled via the bus 3008 to one or more input/output devices 3014. The input device 3014 can include, but is not limited to, a keyboard, mouse, digital pen, microphone, touch screen, gesture recognition system, voice recognition system, imaging device (which may capture eye, hand, head, or body tracking data and/or placement), gamepad, accelerometer, or gyroscope.

Additional Embodiments and Terminology

While the present disclosure discusses example connectors in the medical device and/or patient monitoring context, the apparatuses, systems, and methods described herein may be agnostic to the particular context, and, therefore, may be used in any connector environment. Further, while the present disclosure discusses advantages of the example connectors as including water resistance, other embodiments of devices, apparatuses, systems, and/or methods described herein may not necessarily be water resistant and may have other advantages, as described herein.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conditional language used herein, such as, among others, "can," "might," "may," "e.g.," "for example," and the like, unless specifically stated otherwise, or otherwise understood within the context as used, is generally intended to convey that certain embodiments include, while other embodiments do not include, certain features, elements, or states. Thus, such conditional language is not generally intended to imply that features, elements or states are in any way required for one or more embodiments.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Such disjunctive language is not generally intended to, and should not, imply that certain embodiments require at least one of X, at least one of Y, or at least one of Z to each be present. Thus, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The terms "comprising," "including," "having," and the like are synonymous and are used inclusively, in an open-ended fashion, and do not exclude additional elements, features, acts, operations, and so forth.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others.

What is claimed is:

1. A computer-implemented method for multiprocessing of analyte parameters and analyte monitoring comprising:
   receiving, via a graphical user interface, a request for an analyte history report from a first user computing device;
   in response to receiving the request for the analyte history report,
      querying, from an application programming interface, a set of analyte data entries within a past time window;
      calculating a number of child processes to process the set of analyte data entries;
      determining, from the set of analyte data entries, a first subset of analyte data entries and a second subset of analyte data entries;
      spawning, based at least in part on the number of child processes, (i) a first child process with the first subset of analyte data entries as first input and (ii) a second child process with the second subset of analyte data entries as second input;
      receiving (i) first summary data from the first child process and (ii) second summary data from the second child process;
      combining the first summary data and the second summary data to result in combined summary data; and
      causing presentation, in the graphical user interface, of the analyte history report comprising at least the combined summary data;
   receiving, from the application programming interface, a current analyte data entry;
   causing presentation, in the graphical user interface, of a graphical animated character based at least in part on the current analyte data entry;
   receiving, via the graphical user interface, user input associated with the graphical animated character; and
   storing the user input in a database.

2. The computer-implemented method of claim 1, wherein the first child process is further configured to access data from a secondary data source having behavioral data, and correlate analyte data with the behavioral data within a time window of a data entry from the first subset of analyte data entries.

3. The computer-implemented method of claim 1, further comprising:
   receiving, via a second graphical user interface, textual user input from a second user computing device;
   identifying (i) a first user profile associated with the first user computing device and (ii) a second user profile associated with the first user profile, wherein the second user profile is further associated with the second user computing device;
   determining that the textual user input is directed toward the first user profile;

identifying a mediated question associated with the textual user input;
causing presentation, via the graphical user interface, of the mediated question on the first user computing device;
receiving, via the graphical user interface, a mediated answer in response to the mediated question; and
causing presentation, via the second graphical user interface, of an indication of the mediated answer on the second user computing device.

4. The computer-implemented method of claim 3, wherein identifying the mediated question and causing presentation thereof comprises translating the textual user input from a first user into the grammatical voice of the graphical animated character and presenting it from the animated character to a second user through the graphical user interface.

5. The computer-implemented method of claim 4, further comprising:
generating training data, wherein generating training data further comprises:
converting (i) analyte data and (ii) user input associated with at least one of food or exercise to vector data;
training a recommendation model using the vector data;
providing user input data to the recommendation model;
receiving a recommendation from the recommendation model; and
causing output, in the graphical user interface, based at least in part on the recommendation.

6. The computer-implemented method of claim 5, further comprising:
receiving (i) a challenge setting and (ii) a reward setting;
receiving first analyte data associated at least with a first time;
determining a first result from the first analyte data according to the challenge setting;
receiving second analyte data associated at least with a second time;
determining a second result from the second analyte data according to the challenge setting;
determining that the first analyte data and the second analyte data collectively satisfy the challenge setting; and
in response to determining that the first analyte data and the second analyte data collectively satisfy the challenge setting,
causing presentation, in the graphical user interface, of an indication of a reward according to the reward setting.

7. The computer-implemented method of claim 6, further comprising:
receiving, via the graphical user interface, textual user input;
selecting, from a plurality of textual responses, a first textual response based at least in part on the textual user input; and
causing presentation, in the graphical user interface, of the first textual response.

8. The computer-implemented method of claim 7, wherein selecting, from the plurality of textual responses, the first textual response further comprises:
providing the textual user input to a chat classifier; and
receiving an indication of the first textual response from the chat classifier.

9. The computer-implemented method of claim 8, further comprising:
generating labels from (i) a plurality of questions and (ii) a plurality of answers;
converting the plurality of questions to question vector data; and
training the chat classifier using the question vector data and the labels.

10. A system comprising:
a memory device configured to store instructions; and
a hardware processor configured to execute the instructions to cause the hardware processor to:
receive, via a graphical user interface, a request for an analyte summary report from a first user computing device;
in response to receiving the request for the analyte summary report,
query, from an application programming interface, a set of analyte data entries within a time window;
calculate a number of child processes to process the set of analyte data entries;
determine, from the set of analyte data entries, a first subset of analyte data entries and a second subset of analyte data entries;
spawn, based at least in part on the number of child processes, (i) a first child process with the first subset of analyte data entries as first input and (ii) a second child process with the second subset of analyte data entries as second input;
receive (i) first summary data from the first child process and (ii) second summary data from the second child process;
combine the first summary data and the second summary data to result in combined summary data; and
cause presentation, in the graphical user interface, of the analyte summary report comprising at least the combined summary data;
receive, from the application programming interface, a current analyte data entry; and
cause presentation, in the graphical user interface, of a graphical character based at least in part on the current analyte data entry.

11. The system of claim 10, wherein the hardware processor is configured to execute further instructions to cause the hardware processor to:
receive, via a second graphical user interface, textual user input from a second user computing device;
identify (i) a first user profile associated with the first user computing device and (ii) a second user profile associated with the first user profile, wherein the second user profile is further associated with the second user computing device;
determine that the textual user input is directed towards the first user profile;
identify a mediated question associated with the textual user input;
cause presentation, via the graphical user interface, of the mediated question on the first user computing device;
receive, via the graphical user interface, a mediated answer in response to the mediated question; and
cause presentation, via the second graphical user interface, of an indication of the mediated answer on the second user computing device.

12. The system of claim 10, wherein the hardware processor is configured to execute further instructions to cause the hardware processor to:

generate training data, wherein generating training data further comprises:
    converting (i) analyte data and (ii) user input associated with at least one of food or exercise to vector data;
train a recommendation model using the vector data;
provide user input data to the recommendation model;
receive a recommendation from the recommendation model; and
cause output, in the graphical user interface, based at least in part on the recommendation.

13. The system of claim 12, wherein the hardware processor is configured to execute further instructions to cause the hardware processor to:
    receive (i) a challenge setting and (ii) a reward setting;
    receive first analyte data associated at least with a first time;
    determine a first result from the first analyte data according to the challenge setting;
    receive second analyte data associated at least with a second time;
    determine a second result from the second analyte data according to the challenge setting;
    determine that the first analyte data and the second analyte data collectively satisfy the challenge setting; and
    in response to determining that the first analyte data and the second analyte data collectively satisfy the challenge setting,
    cause presentation, in the graphical user interface, of an indication of a reward according to the reward setting.

14. The system of claim 10, wherein the hardware processor is configured to execute further instructions to cause the hardware processor to:
    receive, via the graphical user interface, textual user input;
    select, from a plurality of textual responses, a first textual response based at least in part on the textual user input; and
    cause presentation, in the graphical user interface, of the first textual response.

15. The system of claim 14, wherein selecting, from the plurality of textual responses, the first textual response further comprises:
    providing the textual user input to a chat classifier; and
    receiving an indication of the first textual response from the chat classifier.

16. The system of claim 15, wherein the hardware processor is configured to execute further instructions to cause the hardware processor to:
    generate labels from (i) a plurality of questions and (ii) a plurality of answers;
    convert the plurality of questions to question vector data; and
    train the chat classifier using the question vector data and the labels.

* * * * *